United States Patent
Amici et al.

(10) Patent No.: US 8,389,494 B2
(45) Date of Patent: Mar. 5, 2013

(54) P185$^{neu}$-ENCODING DNA AND THERAPEUTICAL USES THEREOF

(75) Inventors: Augusto Amici, Camerino (IT); Federica Cavallo, Orbassano (IT); Guido Forni, Orbassano (IT); Cristina Marchini, Camerino (IT)

(73) Assignee: Indena S.p.A., Milan (IT)

( * ) Notice: Subject to any disclaimer, the term of this patent is extended or adjusted under 35 U.S.C. 154(b) by 11 days.

(21) Appl. No.: 13/109,359

(22) Filed: May 17, 2011

(65) Prior Publication Data

US 2011/0245330 A1 Oct. 6, 2011

Related U.S. Application Data

(62) Division of application No. 12/874,619, filed on Sep. 2, 2010, which is a division of application No. 10/574,897, filed as application No. PCT/EP2004/011161 on Oct. 6, 2004, now Pat. No. 7,795,016.

(30) Foreign Application Priority Data

Oct. 9, 2003 (IT) .............................. MI2003A1942

(51) Int. Cl.
*A61K 48/00* (2006.01)

(52) U.S. Cl. ..................................... 514/44 R

(58) Field of Classification Search ........................ None
See application file for complete search history.

(56) References Cited

U.S. PATENT DOCUMENTS 6,653,292 B1  11/2003  Krieg et al.
2011/0245330 A1*  10/2011  Amici et al. ................ 514/44 R

FOREIGN PATENT DOCUMENTS

WO  WO 2004/007734  1/2004

OTHER PUBLICATIONS

Chen Ying et al: "DNA vaccines encoding full-length or truncated Neu induce protective immunity against Neu-expressing mammary tumors" Cancer Research, American Association for Cancer Research, Baltimore, MD, US, vol. 58, No. 9, May 1, 1998, pp. 1965-1971, XP002149613, ISSN: 0008-5472, the whole document.
Amici et al.: "DNA vaccination with 1-13, full-length or truncated Neu induces, protective immunity against the development of spontaneous mammary tumors in HER-2/neu transgenic mice" Gene Therapy, vol. 7, 2000, pp. 703-706, XP002314634, the whole document.
Chu R S et al: "CPG Oligodeoxynucleotides 5,6 Act as Adjuvants That Switch on T Helper 1 (TH1) Immunity" Journal of Experimental Medicine, Tokyo, vol. 186, No. 10, Nov. 1, 1997, pp. 1623-1631, XPOO291O13O, ISSN: 0022-1007, the whole document.
Quaglino Elena et al: "Concordant 1-13 morphologic and gene expression data show that a vaccine halts HER-2/neu preneoplastic lesions." Journal of Clinical Investigation, vol. 113, No. 5, Mar. 2004, pp. 709-717, XP002314635, ISSN: 0021-9738, the whole document.
Coussens, L. et al., "Tyrosine Kinase Receptor with Extensive homology to EGF Receptor Sahers Chromosomal Location with neu Oncogene", 1985, Science, vol. 230, pp. 1132-1139.

* cited by examiner

*Primary Examiner* — Michael Burkhart
(74) *Attorney, Agent, or Firm* — Young & Thompson

(57) ABSTRACT

Methods for inhibiting the formation and growth of a p185$^{neu}$ positive tumor in a subject, and for treating a subject having a p185$^{neu}$ positive tumor, utilizing a DNA vector coding for a chimeric rat/human Her-2/neu/ErbB-2 protein are provided.

11 Claims, 14 Drawing Sheets

SEQUENCE LISTING

<160> NUMBER OF SEQ ID NOS: 43

<210> SEQ ID NO 1
<211> LENGTH: 922
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
ccgggccgga gccgcaatga tcatcatgga gctggcggcc tggtgccgct gggggttcct      60
cctcgccctc ctgcccccg gaatcgcggg ttacctatac atctcagcat ggccggacag     120
cctgcctgac ctcagcgtct tccagaacct gcaagtaatc cggggacgaa ttctgcacaa     180
tggcgcctac tcgctgaccc tgcaagggct gggcatcagc tggctggggc tgcgctcact     240
gagggaactg ggcagtggac tggccctcat ccaccataac acccacctct gcttcgtgca     300
cacggtgccc tgggaccagc tctttcggaa cccgcaccaa gctctgctcc acactgccaa     360
ccggccagag gacgagtgtg tgggcgaggg cctggcctgc caccagctgt gcgcccgagg     420
gcactgctgg ggtccagggc ccacccagtg tgtcaactgc agccagttcc ttcggggcca     480
ggagtgcgtg gaggaatgcc gagtactgca ggggctcccc agggagtatg tgaatgccag     540
gcactgtttg ccgtgccacc ctgagtgtca gccccagaat ggctcagtga cctgttttgg     600
accggaggct gaccagtgtg tggcctgtgc ccactataag gaccctccct tctgcgtggc     660
ccgctgcccc agcggtgtga aacctgacct ctcctacatg cccatctgga gtttccaga     720 tgaggagggc gcatgccagc cttgccccat caactgcacc cactcctgtg tggacctgga     780
tgacaagggc tgccccgccg agcagagagc cagccctctg acgtccatcg tctctgcggt     840
ggttggcatt ctgctggtcg tggtcttggg ggtggtcttt gggatcctca tcaagcgacg     900
gcagcagaag atccggaagt aa                                              922

<210> SEQ ID NO 2

```
<211> LENGTH: 2083
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
```

| | | | | | |
|---|---|---|---|---|---|
| ccgggccgga | gccgcaatga | tcatcatgga | gctggcggcc | tggtgccgct | ggggggttcct    60 |
| cctcgccctc | ctgcccccg  | gaatcgcggg | cacccaagtg | tgtaccggca | cagacatgaa   120 |
| gttgcggctc | cctgccagtc | ctgagaccca | cctggacatg | ctccgccacc | tgtaccaggg   180 |
| ctgtcaggta | gtgcagggca | acttggagct | tacctacgtg | cctgccaatg | ccagcctctc   240 |
| attcctgcag | gacatccagg | aagttcaggg | ttacatgctc | atcgctcaca | accaggtgaa   300 |
| gcgcgtccca | ctgcaaaggc | tgcgcatcgt | gagagggacc | cagctctttg | aggacaagta   360 |
| tgccctggct | gtgctagaca | accgagatcc | tcaggacaat | gtcgccgcct | ccaccccagg   420 |
| cagaacccca | gagggctgc  | gggagctgca | gcttcgaagt | ctcacagaga | tcctgaaggg   480 |
| aggagttttg | atccgtggga | accctcagct | ctgctaccag | gacatggttt | tgtggaagga   540 |
| cgtcttccgc | aagaataacc | aactggctcc | tgtcgatata | gacaccaatc | gttcccgggc   600 |
| ctgtccacct | tgtgccccg  | cctgcaaaga | caatcactgt | tggggtgaga | gtccggaaga   660 |
| ctgtcagatc | ttgactggca | ccatctgtac | cagtggttgt | gcccggtgca | agggccggct   720 |
| gcccactgac | tgctgccatg | agcagtgtgc | cgcaggctgc | acgggcccca | agcattctga   780 |
| ctgcctggcc | tgcctccact | tcaatcatag | tggtatctgt | gagctgcact | gcccagccct   840 |
| cgtcacctac | aacacagaca | cctttgagtc | catgcacaac | cctgagggtc | gctacacctt   900 |
| tggtgccagc | tgcgtgacca | cctgccccta | caactacctg | tctacggaag | tgggatcctg   960 |
| cactctggtg | tgtcccccga | ataaccaaga | ggtcacagct | gaggacggaa | cacagcgttg  1020 |
| tgagaaatgc | agcaagccct | gtgctcgagt | gtgctatggt | ctgggcatgg | agcaccttcg  1080 |
| agggggcgagg | gccatcacca | gtgacaatgt | ccaggagttt | gatggctgca | agaagatctt  1140 |
| tgggagcctg | gcatttttgc | cggagagctt | tgatggggac | ccctcctccg | gcattgctcc  1200 |
| gctgaggcct | gagcagctcc | aagtgttcga | aaccctggag | gagatcacag | gttacctata  1260 |
| catctcagca | tggccggaca | gcctgcctga | cctcagcgtc | ttccagaacc | tgcaagtaat  1320 |
| ccggggacga | attctgcaca | atggcgccta | ctcgctgacc | ctgcaagggc | tgggcatcag  1380 |
| ctggctgggg | ctgcgctcac | tgagggaact | gggcagtgga | ctggcctca  | tccaccataa  1440 |
| cacccacctc | tgcttcgtgc | acacggtgcc | ctggaccag  | ctctttcgga | acccgcacca  1500 |
| agctctgctc | cacactgcca | accggccaga | ggacagtgt  | gtgggcgagg | gcctggcctg  1560 |
| ccaccagctg | tgcgcccgag | ggcactgctg | gggtccaggg | cccacccagt | gtgtcaactg  1620 |
| cagccagttc | cttcggggcc | aggagtgcgt | ggaggaatgc | cgagtactgc | aggggctccc  1680 |
| cagggagtat | gtgaatgcca | ggcactgttt | gccgtgccac | cctgagtgtc | agccccagaa  1740 |
| tggctcagtg | acctgttttg | gaccggaggc | tgaccagtgt | gtggcctgtg | cccactataa  1800 |
| ggaccctccc | ttctgcgtgg | cccgctgccc | cagcggtgtg | aaacctgacc | tctcctacat  1860 |
| gcccatctgg | aagtttccag | atgaggaggg | cgcatgccag | ccttgcccca | tcaactgcac  1920 |
| ccactcctgt | gtggacctgg | atgacaaggg | ctgccccgcc | gagcagagag | ccagccctct  1980 |
| gacgtccatc | gtctctgcgg | tggttggcat | tctgctggtc | gtggtcttgg | gggtggtctt  2040 |
| tgggatcctc | atcaagcgac | ggcagcagaa | gatccggaag | taa        2083 |

<210> SEQ ID NO 3
<211> LENGTH: 1939
<212> TYPE: DNA
<213> ORGANISM: Artificial Sequence
<220> FEATURE:
<223> OTHER INFORMATION: Description of Artificial Sequence: Synthetic construct

<400> SEQUENCE: 3

```
ccgggccgga gccgcaatga tcatcatgga gctggcggcc tggtgccgct gggggttcct      60
cctcgccctc ctgcccccg  aatcgcggc  tagcctgtcc ttcctgcagg atatccagga     120
ggtgcagggc tacgtgctca tcgctcacaa ccaagtgagg caggtcccac tgcagaggct     180
gcggattgtg cgaggcaccc agctctttga ggacaactat gccctggccg tgctagacaa     240
tggagacccg ctgaacaata ccaccccctgt cacaggggcc tccccaggag cctgcgggga    300
gctgcagctt cgaagcctca cagagatctt gaaaggaggg gtcttgatcc agcggaaccc     360
ccagctctgc taccaggaca cgattttgtg gaaggacatc ttccacaaga caaccagct     420
ggctctcaca ctgatagaca ccaaccgctc tcgggcctgc caccctgtt  ctccgatgtg     480
taagggctcc cgctgctggg gagagagttc tgaggattgt cagagcctga cgcgcactgt     540
ctgtgccggt ggctgtgccc gctgcaaggg gccactgccc actgactgct gccatgagca     600
gtgtgctgcc ggctgcacgg gccccaagca ctctgactgc ctggcctgcc tccacttcaa     660
ccacagtggc atctgtgagc tgcactgccc agccctggtc acctacaaca cagacacgtt     720
tgagtccatg cccaatcccg agggccggta tacattcggc gccagctgtg tgactgcctg     780
tccctacaac tacctttcta cggacgtggg atcctgcacc ctcgtctgcc ccctgcacaa     840
ccaagaggtg acagcagagg atggaacaca gcggtgtgag aagtgcagca agccctgtgc     900
ccgagtgtgc tatggtctgg gcatggagca cttgcgagag gtgagggcag ttaccagtgc     960
caatatccag gagtttgctg gctgcaagaa gatctttggg agcctggcat ttctgccgga    1020
gagctttgat ggggacccag cctccaacac tgccccgctc cagccagagc agctccaagt    1080
gtttgagact ctggaagaga tcacaggtta cctatacatc tcagcatggc cggacagcct    1140
gcctgacctc agcgtcttcc agaacctgca agtaatccgg ggacgaattc tgcacaatgg    1200
cgcctactcg ctgaccctgc aagggctggg catcagctgg ctgggctgc  gctcactgag    1260
ggaactgggc agtggactgg ccctcatcca ccataacacc cacctctgct tcgtgcacac    1320
ggtgccctgg gaccagctct ttcggaaccc gcaccaagct ctgctccaca ctgccaaccg    1380
gccagaggac gagtgtgtgg gcgagggcct ggcctgccac cagctgtgcg cccgagggca    1440
ctgctgggt  ccagggccca cccagtgtgt caactgcagc cagttccttc ggggccagga    1500
gtgcgtggag gaatgccgag tactgcaggg gctccccagg gagtatgtga atgccaggca    1560
ctgtttgccg tgccaccctg agtgtcagcc ccagaatggc tcagtgacct gttttggacc    1620
ggaggctgac cagtgtgtgg cctgtgccca ctataaggac cctccttct  gcgtggcccg    1680
ctgccccagc ggtgtgaaac ctgacctctc ctacatgccc atctggaagt tccagatga   1740
ggagggcgca tgccagcctt gccccatcaa ctgcacccac tcctgtgtgg acctggatga   1800
caagggctgc cccgccgagc agagagccag ccctctgacg tccatcgtct ctgcggtggt   1860
tggcattctg ctggtcgtgg tcttgggggt ggtctttggg atcctcatca agcgacggca   1920
gcagaagatc cggaagtaa                                                 1939
```

<210> SEQ ID NO 4
<211> LENGTH: 1699
<212> TYPE: DNA

<213> ORGANISM: Artificial Sequence
<220> FEATURE:
<223> OTHER INFORMATION: Description of Artificial Sequence: Synthetic
      construct

<400> SEQUENCE: 4

| ccgggccgga | gccgcaatga | tcatcatgga | gctggcggcc | tggtgccgct | ggggggttcct | 60 |
| cctcgccctc | ctgccccccg | gaatcgcggc | tagcggaggg | gtcttgatcc | agcggaaccc | 120 |
| ccagctctgc | taccaggaca | cgattttgtg | gaaggacatc | ttccacaaga | caaccagct | 180 |
| ggctctcaca | ctgatagaca | ccaaccgctc | tcgggcctgc | cacccctgtt | ctccgatgtg | 240 |
| taagggctcc | cgctgctggg | gagagagttc | tgaggattgt | cagagcctga | cgcgcactgt | 300 |
| ctgtgccggt | ggctgtgccc | gctgcaaggg | gccactgccc | actgactgct | gccatgagca | 360 |
| gtgtgctgcc | ggctgcacgg | gccccaagca | ctctgactgc | ctggcctgcc | tccacttcaa | 420 |
| ccacagtggc | atctgtgagc | tgcactgccc | agccctggtc | acctacaaca | cagacacgtt | 480 |
| tgagtccatg | cccaatcccg | agggccggta | tacattcggc | ccagctgtg | tgactgcctg | 540 |
| tccctacaac | tacctttcta | cggacgtggg | atcctgcacc | ctcgtctgcc | ccctgcacaa | 600 |
| ccaagaggtg | acagcagagg | atggaacaca | gcggtgtgag | aagtgcagca | gccctgtgc | 660 |
| ccgagtgtgc | tatggtctgg | gcatggagca | cttgcgagag | gtgagggcag | ttaccagtgc | 720 |
| caatatccag | gagtttgctg | gctgcaagaa | gatctttggg | agcctggcat | ttctgccgga | 780 |
| gagctttgat | ggggacccag | cctccaacac | tgccccgctc | cagccagagc | agctccaagt | 840 |
| gtttgagact | ctggaagaga | tcacaggtta | cctatacatc | tcagcatggc | cggacagcct | 900 |
| gcctgacctc | agcgtcttcc | agaacctgca | agtaatccgg | ggacgaattc | tgcacaatgg | 960 |
| cgcctactcg | ctgaccctgc | aagggctggg | catcagctgg | ctggggctgc | gctcactgag | 1020 |
| ggaactgggc | agtggactgg | ccctcatcca | ccataacacc | cacctctgct | tcgtgcacac | 1080 |
| ggtgccctgg | gaccagctct | ttcggaaccc | gcaccaagct | ctgctccaca | ctgccaaccg | 1140 |
| gccagaggac | gagtgtgtgg | gcgagggcct | ggcctgccac | cagctgtgcg | cccgagggca | 1200 |
| ctgctggggt | ccagggccca | cccagtgtgt | caactgcagc | cagttccttc | ggggccagga | 1260 |
| gtgcgtggag | gaatgccgag | tactgcaggg | gctccccagg | gagtatgtga | atgccaggca | 1320 |
| ctgtttgccg | tgccacccctg | agtgtcagcc | ccagaatggc | tcagtgacct | gttttggacc | 1380 |
| ggaggctgac | cagtgtgtgg | cctgtgccca | ctataaggac | cctcccttct | gcgtggcccg | 1440 |
| ctgccccagc | ggtgtgaaac | ctgacctctc | ctacatgccc | atctggaagt | ttccagatga | 1500 |
| ggagggcgca | tgccagcctt | gccccatcaa | ctgcacccac | tcctgtgtgg | acctggatga | 1560 |
| caagggctgc | cccgccgagc | agagagccag | ccctctgacg | tccatcgtct | gcgggtggt | 1620 |
| tggcattctg | ctggtcgtgg | tcttgggggt | ggtctttggg | atcctcatca | gcgacggca | 1680 |
| gcagaagatc | cggaagtaa | | | | | 1699 |

<210> SEQ ID NO 5
<211> LENGTH: 1459
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5

| ccgggccgga | gccgcaatga | tcatcatgga | gctggcggcc | tggtgccgct | ggggggttcct | 60 |
| cctcgccctc | ctgccccccg | gaatcgcggc | tagcctgccc | actgactgct | gccatgagca | 120 |

```
gtgtgctgcc ggctgcacgg gccccaagca ctctgactgc ctggcctgcc tccacttcaa    180
ccacagtggc atctgtgagc tgcactgccc agccctggtc acctacaaca cagacacgtt    240
tgagtccatg cccaatcccg agggccggta tacattcggc gccagctgtg tgactgcctg    300
tccctacaac tacctttcta cggacgtggg atcctgcacc ctcgtctgcc ccctgcacaa    360
ccaagaggtg acagcagagg atggaacaca gcggtgtgag aagtgcagca agccctgtgc    420
ccgagtgtgt tatggtctgg gcatggagca cttgcgagag gtgagggcag ttaccagtgc    480
caatatccag gagtttgctg gctgcaagaa gatctttggg agcctggcat ttctgccgga    540
gagctttgat ggggacccag cctccaacac tgccccgctc cagccagagc agctccaagt    600
gtttgagact ctggaagaga tcacaggtta cctatacatc tcagcatggc cggacagcct    660
gcctgacctc agcgtcttcc agaacctgca agtaatccgg ggacgaattc tgcacaatgg    720
cgcctactcg ctgaccctgc aagggctggg catcagctgg ctggggctgc gctcactgag    780
ggaactgggc agtggactgg ccctcatcca ccataacacc cacctctgct tcgtgcacac    840
ggtgccctgg gaccagctct ttcggaaccc gcaccaagct ctgctccaca ctgccaaccg    900
gccagaggac gagtgtgtgg gcgagggcct ggcctgccac cagctgtgcg cccgagggca    960
ctgctggggt ccagggccca cccagtgtgt caactgcagc cagttccttc ggggccagga   1020
gtgcgtggag gaatgccgag tactgcaggg gctcccagg gagtatgtga atgccaggca   1080
ctgtttgccg tgccaccctg agtgtcagcc ccagaatggc tcagtgacct gttttggacc   1140
ggaggctgac cagtgtgtgg cctgtgccca ctataaggac cctcccttct gcgtggcccg   1200
ctgccccagc ggtgtgaaac ctgacctctc ctacatgccc atctggaagt ttccagatga   1260
ggagggcgca tgccagcctt gccccatcaa ctgcacccac tcctgtgtgg acctggatga   1320
caagggctgc cccgccgagc agagagccag ccctctgacg tccatcgtct ctgcggtggt   1380
tggcattctg ctggtcgtgg tcttgggggt ggtctttggg atcctcatca agcgacggca   1440
gcagaagatc cggaagtaa                                                 1459

<210> SEQ ID NO 6
<211> LENGTH: 1219
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6
ccgggccgga gccgcaatga tcatcatgga gctggcggcc tggtgccgct ggggggttcct    60 cctcgccctc ctgcccccccg gaatcgcggc tagctgcacc ctcgtctgcc ccctgcacaa   120
ccaagaggtg acagcagagg atggaacaca gcggtgtgag aagtgcagca agccctgtgc   180
ccgagtgtgc tatggtctgg gcatggagca cttgcgagag gtgagggcag ttaccagtgc   240
caatatccag gagtttgctg gctgcaagaa gatctttggg agcctggcat ttctgccgga   300
gagctttgat ggggacccag cctccaacac tgccccgctc cagccagagc agctccaagt   360
gtttgagact ctggaagaga tcacaggtta cctatacatc tcagcatggc cggacagcct   420
gcctgacctc agcgtcttcc agaacctgca agtaatccgg ggacgaattc tgcacaatgg   480
cgcctactcg ctgaccctgc aagggctggg catcagctgg ctggggctgc gctcactgag   540
ggaactgggc agtggactgg ccctcatcca ccataacacc cacctctgct tcgtgcacac   600
ggtgccctgg gaccagctct ttcggaaccc gcaccaagct ctgctccaca ctgccaaccg   660
gccagaggac gagtgtgtgg gcgagggcct ggcctgccac cagctgtgcg cccgagggca   720
```

```
ctgctggggt ccagggccca cccagtgtgt caactgcagc cagttccttc ggggccagga      780
gtgcgtggag gaatgccgag tactgcaggg gctccccagg gagtatgtga atgccaggca      840
ctgtttgccg tgccaccctg agtgtcagcc cagaatggc tcagtgacct gttttggacc       900
ggaggctgac cagtgtgtgg cctgtgccca ctataaggac cctcccttct gcgtggcccg      960
ctgccccagc ggtgtgaaac ctgacctctc ctacatgccc atctggaagt ttccagatga     1020
ggagggcgca tgccagcctt gccccatcaa ctgcacccac tcctgtgtgg acctggatga     1080
caagggctgc cccgccgagc agagagccag ccctctgacg tccatcgtct ctgcggtggt     1140
tggcattctg ctggtcgtgg tcttgggggt ggtctttggg atcctcatca agcgacggca     1200
gcagaagatc cggaagtaa                                                  1219
```

<210> SEQ ID NO 7
<211> LENGTH: 979
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7

```
ccgggccgga gccgcaatga tcatcatgga gctggcggcc tggtgccgct gggggttcct       60
cctcgccctc ctgcccccg gaatcgcggc tagcccgctc cagccagagc agctccaagt      120
gtttgagact ctggaagaga tcacaggtta cctatacatc tcagcatggc cggacagcct     180
gcctgacctc agcgtcttcc agaacctgca agtaatccgg ggacgaattc tgcacaatgg     240
cgcctactcg ctgaccctgc aagggctggg catcagctgg ctggggctgc gctcactgag     300
ggaactgggc agtggactgg ccctcatcca ccataacacc cacctctgct tcgtgcacac     360
ggtgccctgg gaccagctct ttcggaaccc gcaccaagct ctgctccaca ctgccaaccg     420
gccagaggac gagtgtgtgg gcgagggcct ggcctgccac cagctgtgcg cccgagggca     480
ctgctggggt ccagggccca cccagtgtgt caactgcagc cagttccttc ggggccagga     540
gtgcgtggag gaatgccgag tactgcaggg gctccccagg gagtatgtga atgccaggca     600
ctgtttgccg tgccaccctg agtgtcagcc cagaatggc tcagtgacct gttttggacc      660
ggaggctgac cagtgtgtgg cctgtgccca ctataaggac cctcccttct gcgtggcccg     720
ctgccccagc ggtgtgaaac ctgacctctc ctacatgccc atctggaagt ttccagatga     780
ggagggcgca tgccagcctt gccccatcaa ctgcacccac tcctgtgtgg acctggatga     840
caagggctgc cccgccgagc agagagccag ccctctgacg tccatcgtct ctgcggtggt     900
tggcattctg ctggtcgtgg tcttgggggt ggtctttggg atcctcatca agcgacggca     960
gcagaagatc cggaagtaa                                                  979
```

<210> SEQ ID NO 8
<211> LENGTH: 739
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 8

```
ccgggccgga gccgcaatga tcatcatgga gctggcggcc tggtgccgct gggggttcct       60
cctcgccctc ctgcccccg gaatcgcggc tagcaacacc cacctctgct tcgtgcacac      120
ggtgccctgg gaccagctct ttcggaaccc gcaccaagct ctgctccaca ctgccaaccg     180
```

```
gccagaggac gagtgtgtgg gcgagggcct ggcctgccac cagctgtgcg cccgagggca    240
ctgctggggt ccagggccca cccagtgtgt caactgcagc cagttccttc ggggccagga    300
gtgcgtggag gaatgccgag tactgcaggg gctccccagg gagtatgtga atgccaggca    360
ctgtttgccg tgccaccctg agtgtcagcc ccagaatggc tcagtgacct gttttggacc    420
ggaggctgac cagtgtgtgg cctgtgccca ctataaggac cctcccttct gcgtggcccg    480
ctgccccagc ggtgtgaaac ctgacctctc ctacatgccc atctggaagt tccagatga    540 ggagggcgca tgccagcctt gccccatcaa ctgcacccac tcctgtgtgg acctggatga    600
caagggctgc cccgccgagc agagagccag ccctctgacg tccatcgtct ctgcggtggt    660
tggcattctg ctggtcgtgg tcttgggggt ggtctttggg atcctcatca agcgacggca    720
gcagaagatc cggaagtaa                                                739

<210> SEQ ID NO 9
<211> LENGTH: 499
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9
ccgggccgga gccgcaatga tcatcatgga gctggcggcc tggtgccgct ggggggttcct    60 cctcgccctc ctgccccccg gaatcgcggc tagccccagg gagtatgtga atgccaggca   120
ctgtttgccg tgccaccctg agtgtcagcc ccagaatggc tcagtgacct gttttggacc   180
ggaggctgac cagtgtgtgg cctgtgccca ctataaggac cctcccttct gcgtggcccg   240
ctgccccagc ggtgtgaaac ctgacctctc ctacatgccc atctggaagt tccagatga   300 ggagggcgca tgccagcctt gccccatcaa ctgcacccac tcctgtgtgg acctggatga   360
caagggctgc cccgccgagc agagagccag ccctctgacg tccatcgtct ctgcggtggt   420
tggcattctg ctggtcgtgg tcttgggggt ggtctttggg atcctcatca agcgacggca   480
gcagaagatc cggaagtaa                                                499

<210> SEQ ID NO 10
<211> LENGTH: 2086
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
ccgggccgga gccgcaatga tcatcatgga gctggcggcc tggtgccgct ggggggttcct    60 cctcgccctc ctgccccccg gaatcgcggg cacccaagtg tgtaccggca cagacatgaa   120
gttgcggctc cctgccagtc ctgagaccca cctggacatg ctccgccacc tgtaccaggg   180
ctgtcaggta gtgcagggca acttggagct tacctacgtg cctgccaatg ccagcgctag   240
cctgtccttc ctgcaggata tccaggaggt gcagggctac gtgctcatcg ctcacaacca   300
agtgaggcag gtcccactgc agaggctgcg gattgtgcga ggcacccagc tctttgagga   360
caactatgcc ctggccgtgc tagacaatgg agacccgctg aacaatacca ccctgtcac   420 aggggcctcc ccaggaggcc tgcgggagct gcagcttcga agcctcacag agatcttgaa   480 aggagggggtt ttgatccagc ggaaccccca gctctgctac caggacacga ttttgtggaa   540
ggacatcttc cacaagaaca accagctggc tctcacactg atagacacca accgctctcg   600
```

```
ggcctgccac ccctgttctc cgatgtgtaa gggctcccgc tgctggggag agagttctga      660
ggattgtcag agcctgacgc gcactgtctg tgccggtggc tgtgcccgct gcaaggggcc      720
actgcccact gactgctgcc atgagcagtg tgctgccggc tgcacgggcc caagcactc       780 tgactgcctg gcctgcctcc acttcaacca cagtggcatc tgtgagctgc actgcccagc      840
cctggtcacc tacaacacag acacgtttga gtccatgccc aatcccgagg ccggtatac       900 attcggcgcc agctgtgtga ctgcctgtcc ctacaactac ctttctacgg acgtgggatc      960
ctgcaccctc gtctgccccc tgcacaacca gaggtgaca gcagaggatg aacacagcg       1020 gtgtgagaag tgcagcaagc cctgtgcccg agtgtgctat ggtctgggca tggagcactt    1080
gcgagaggtg agggcagtta ccagtgccaa tatccaggag tttgctggct gcaagaagat    1140 cttttgggagc ctggcatttc tgccggagag ctttgatggg gacccagcct ccaacactgc    1200
cccgctccag ccagagcagc tccaagtgtt tgagactctg aagagatca caggttacct     1260 atacatctca gcatggccgg acagcctgcc tgacctcagc gtcttccaga acctgcaagt    1320
aatccgggga cgaattctgc acaatggcgc ctactcgctg accctgcaag ggctgggcat    1380
cagctggctg gggctgcgct cactgaggga actgggcagt ggactggccc tcatccacca    1440
taacacccac ctctgcttcg tgcacacggt gccctgggac cagctctttc ggaacccgca    1500
ccaagctctg ctccacactg ccaaccgcc agaggacgag tgtgtgggcg agggcctggc    1560
ctgccaccag ctgtgcgccc gagggcactg ctgggtcca gggcccaccc agtgtgtcaa    1620
ctgcagccag ttccttcggg gccagagtg cgtggaggaa tgccgagtac tgcaggggct    1680
ccccagggag tatgtgaatg ccaggcactg tttgccgtgc caccctgagt gtcagcccca    1740
gaatggctca gtgacctgtt ttggaccgga ggctgaccag tgtgtggcct gtgcccacta    1800
taaggaccct cccttctgcg tggcccgctg ccccagcggt gtgaaacctg acctctccta    1860
catgcccatc tggaagtttc cagatgagga gggcgcatgc cagccttgcc ccatcaactg    1920 caccccactcc tgtgtggacc tggatgacaa gggctgcccc gccgagcaga gagccagccc   1980
tctgacgtcc atcgtctctg cggtggttgg cattctgctg gtcgtggtct tgggggtggt    2040
ctttgggatc ctcatcaagc gacggcagca gaagatccgg aagtaa                   2086
```

<210> SEQ ID NO 11
<211> LENGTH: 2086
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11

```
ccgggccgga gccgcaatga tcatcatgga gctggcggcc tggtgccgct gggggttcct       60
cctcgccctc ctgcccccg gaatcgcggg caccaagtg tgtaccggca cagacatgaa       120
gttgcggctc cctgccagtc ctgagaccca cctggacatg ctccgccacc tgtaccaggg      180
ctgtcaggta gtgcagggca acttggagct tacctacgtg cctgccaatg ccagcctctc      240
attcctgcag gacatccagg aagttcaggg ttacatgctc atcgctcaca accaggtgaa      300
gcgcgtccca ctgcaaaggc tgcgcatcgt gagagggacc cagctctttg aggacaagta      360
tgccctggct gtgctagaca accgagatcc tcaggacaat gtgccgcct ccaccccagg      420 cagaacccca gaggggctgc gggagctgca gcttcgaagt ctcacagaga tcctggctag     480 cggagggggtc ttgatccagc ggaacccca gctctgctac caggacacga ttttgtggaa    540
```

```
ggacatcttc cacaagaaca accagctggc tctcacactg atagacacca accgctctcg    600
ggcctgccac ccctgttctc cgatgtgtaa gggctcccgc tgctggggag agagttctga    660
ggattgtcag agcctgacgc gcactgtctg tgccggtggc tgtgcccgct gcaaggggcc    720
actgcccact gactgctgcc atgagcagtg tgctgccggc tgcacgggcc caagcactc     780 tgactgcctg gcctgcctcc acttcaacca cagtggcatc tgtgagctgc actgcccagc    840
cctggtcacc tacaacacag acacgtttga gtccatgccc aatcccgagg gccggtatac    900
attcggcgcc agctgtgtga ctgcctgtcc ctacaactac ctttctacgg acgtgggatc    960 ctgcacccte gtctgccccc tgcacaacca agaggtgaca gcagaggatg aacacagcg    1020 gtgtgagaag tgcagcaagc cctgtgcccg agtgtgctat ggtctgggca tggagcactt   1080
gcgagaggtg agggcagtta ccagtgccaa tatccaggag tttgctggct gcaagaagat   1140
ctttgggagc ctggcatttc tgccggagag ctttgatggg acccagcct ccaacactgc    1200 cccgctccag ccagagcagc tccaagtgtt tgagactctg aagagatca caggttacct   1260 atacatctca gcatggccgg acagcctgcc tgacctcagc gtcttccaga acctgcaagt   1320
aatccgggga cgaattctgc acaatggcgc ctactcgctg accctgcaag gctgggcat    1380 cagctggctg gggctgcgct cactgaggga actgggcagt ggactggccc tcatccacca   1440
taacacccac ctctgcttcg tgcacacggt gccctgggac cagctctttc ggaacccgca   1500
ccaagctctg ctccacactg ccaaccggcc agaggacgag tgtgtgggcg agggcctggc   1560
ctgccaccag ctgtgcgccc gagggcactg ctggggtcca gggcccaccc agtgtgtcaa   1620
ctgcagccag ttccttcggg gccaggagtg cgtggaggaa tgccgagtac tgcaggggct   1680
ccccagggag tatgtgaatg ccaggcactg tttgccgtgc cacccctgagt gtcagcccca   1740 gaatggctca gtgacctgtt ttggaccgga ggctgaccag tgtgtggcct gtgcccacta   1800
taaggaccct cccttctgcg tggcccgctg ccccagcggt gtgaaaccctg acctctccta   1860 catgcccatc tggaagtttc cagatgagga gggcgcatgc cagcccttgcc ccatcaactg   1920 cacccactcc tgtgtggacc tggatgacaa gggctgcccc gccgagcaga gagccagccc   1980
tctgacgtcc atcgtctctg cggtggttgg cattctgctg gtcgtggtct tggggtggt    2040 ctttgggatc ctcatcaagc gacggcagca aagatccgg aagtaa                   2086
```

<210> SEQ ID NO 12
<211> LENGTH: 2086
<212> TYPE: DNA
<213> ORGANISM: Artificial Sequence
<220> FEATURE:
<223> OTHER INFORMATION: Description of Artificial Sequence: Synthetic
      construct <400> SEQUENCE: 12

```
ccgggccgga gccgcaatga tcatcatgga gctggcggcc tggtgccgct gggggttcct     60
cctcgccctc ctgcccccg gaatcgcggg cacccaagtg tgtaccggca cagacatgaa    120
gttgcggctc cctgccagtc ctgagaccca cctggacatg ctccgccacc tgtaccaggg    180
ctgtcaggta gtgcagggca acttggagct tacctacgtg cctgccaatg ccagcctctc    240
attcctgcag gacatccagg aagttcaggg ttacatgctc atcgctcaca accaggtgaa    300
gcgcgtccca ctgcaaaggc tgcgcatcgt gagagggacc cagctctttg aggacaagta    360
tgccctggct gtgctagaca accgagatcc tcaggacaat gtcgccgcct ccaccccagg    420
cagaacccca gaggggctgc gggagctgca gcttcgaagt ctcacagaga tcctgaaggg    480
aggagttttg atccgtggga acccatcagct ctgctaccag gacatggttt tgtggaagga   540
```

```
cgtcttccgc aagaataacc aactggctcc tgtcgatata gacaccaatc gttcccgggc      600
ctgtccacct tgtgccccg cctgcaaaga caatcactgt tggggtgaga gtccggaaga      660
ctgtcagatc ttgactggca ccatctgtac cagtggttgt gcccggtgca agggcgctag      720
cctgcccact gactgctgcc atgagcagtg tgctgccggc tgcacgggcc ccaagcactc      780
tgactgcctg gcctgcctcc acttcaacca cagtggcatc tgtgagctgc actgcccagc      840
cctggtcacc tacaacacag acacgtttga gtccatgccc aatcccgagg gccggtatac      900
attcggcgcc agctgtgtga ctgcctgtcc ctacaactac ctttctacgg acgtgggatc      960
ctgcaccctc gtctgccccc tgcacaacca agaggtgaca gcagaggatg aacacagcg     1020 gtgtgagaag tgcagcaagc cctgtgcccg agtgtgctat ggtctgggca tggagcactt     1080
gcgagaggtg agggcagtta ccagtgccaa tatccaggag tttgctggct gcaagaagat     1140
ctttgggagc ctggcatttc tgccggagag ctttgatggg acccagcct ccaacactgc     1200 cccgctccag ccagagcagc tccaagtgtt tgagactctg gaagagatca caggttacct     1260
atacatctca gcatggccgg acagcctgcc tgacctcagc gtcttccaga acctgcaagt     1320
aatccgggga cgaattctgc acaatggcgc ctactcgctg accctgcaag ggctgggcat     1380
cagctggctg gggctgcgct cactgaggga actgggcagt ggactggccc tcatccacca     1440
taacacccac ctctgcttcg tgcacacggt gccctgggac cagctctttc ggaacccgca     1500
ccaagctctg ctccacactg ccaaccggcc agaggacgag tgtgtgggcg agggcctggc     1560
ctgccaccag ctgtgcgccc gagggcactg ctggggtcca gggcccaccc agtgtgtcaa     1620
ctgcagccag ttccttcggg gccaggagtg cgtggaggaa tgccgagtac tgcaggggct     1680 ccccaggag tatgtgaatg ccaggcactg tttgccgtgc cacctgagt gtcagcccca     1740 gaatggctca gtgacctgtt ttggaccgga ggctgaccag tgtgtggcct gtgcccacta     1800 taaggacct cccttctgcg tggcccgctg ccccagcggt gtgaaacctg acctctccta     1860
catgcccatc tggaagtttc cagatgagga gggcgcatgc cagccttgcc ccatcaactg     1920
cacccactcc tgtgtggacc tggatgacaa gggctgcccc gccgagcaga gagccagccc     1980
tctgacgtcc atcgtctctg cggtggttgg cattctgctg gtcgtggtct tgggggtggt     2040
ctttgggatc ctcatcaagc gacggcagca gaagatccgg aagtaa                    2086
```

<210> SEQ ID NO 13
<211> LENGTH: 2086
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13

```
ccgggccgga gccgcaatga tcatcatgga gctggcggcc tggtgccgct gggggttcct       60
cctcgccctc ctgccccccg gaatcgcggg cacccaagtg tgtaccggca cagacatgaa     120
gttgcggctc cctgccagtc ctgagaccca cctggacatg ctccgccacc tgtaccaggg     180
ctgtcaggta gtgcagggca acttggagct tacctacgtg cctgccaatg ccagcctctc     240
attcctgcag gacatccagg aagttcaggg ttacatgctc atcgctcaca accaggtgaa     300
gcgcgtccca ctgcaaaggc tgcgcatcgt gagagggacc cagctctttg aggacaagta     360
tgccctggct gtgctagaca accgagatcc tcaggacaat gtcgccgcct ccaccccagg     420
cagaacccca gaggggctgc gggagctgca gcttcgaagt ctcacagaga tcctgaaggg     480
```

```
aggagttttg atccgtggga accctcagct ctgctaccag gacatggttt tgtggaagga    540
cgtcttccgc aagaataacc aactggctcc tgtcgatata gacaccaatc gttcccgggc    600
ctgtccacct tgtgccccg  cctgcaaaga caatcactgt tggggtgaga gtccggaaga    660
ctgtcagatc ttgactggca ccatctgtac cagtggttgt gcccggtgca agggccggct    720
gcccactgac tgctgccatg agcagtgtgc cgcaggctgc acgggcccca agcattctga    780
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggagctag    960 ctgcacccte gtctgccccc tgcacaacca agaggtgaca gcagaggatg aacacagcg    1020 gtgtgagaag tgcagcaagc cctgtgcccg agtgtgctat ggtctgggca tggagcactt   1080
gcgagaggtg agggcagtta ccagtgccaa tatccaggag tttgctggct gcaagaagat   1140
ctttgggagc ctggcatttc tgccggagag ctttgatggg acccagcct  caacactgc    1200 cccgctccag ccagagcagc tccaagtgtt tgagactctg aagagatca  caggttacct   1260 atacatctca gcatggccgg acagcctgcc tgacctcagc gtcttccaga acctgcaagt   1320
aatccgggga cgaattctgc acaatggcgc ctactcgctg accctgcaag gctgggcat    1380 cagctggctg gggctgcgct cactgaggga actgggcagt ggactggccc tcatccacca   1440
taacacccac ctctgcttcg tgcacacggt gccctgggac cagctcttc  ggaacccgca   1500 ccaagctctg ctccacactg ccaaccggcc agaggacgag tgtgtgggcg agggcctggc   1560
ctgccaccag ctgtgcgccc gagggcactg ctggggtcca gggcccaccc agtgtgtcaa   1620
ctgcagccag ttccttcggg gccaggagtg cgtggaggaa tgccgagtac tgcaggggct   1680
ccccagggag tatgtgaatg ccaggcactg tttgccgtgc caccctgagt gtcagcccca   1740
gaatggctca gtgacctgtt ttggaccgga ggctgaccag tgtgtggcct gtgcccacta   1800
taaggaccct cccttctgcg tggcccgctg ccccagcggt gtgaaacctg acctctccta   1860
catgcccatc tggaagtttc cagatgagga gggcgcatgc cagccttgcc ccatcaactg   1920
cacccactcc tgtgtggacc tggatgacaa gggctgcccc gccgagcaga gagccagccc   1980
tctgacgtcc atcgtctctg cggtggttgg cattctgctg gtcgtggtct gggggtggt    2040 ctttgggatc ctcatcaagc gacggcagca gaagatccgg aagtaa                  2086
```

<210> SEQ ID NO 14
<211> LENGTH: 2086
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14

```
ccgggccgga gccgcaatga tcatcatgga gctggcggcc tggtgccgct ggggggttcct    60 cctcgccctc ctgccccccg gaatcgcggg cacccaagtg tgtaccggca cagacatgaa   120
gttgcggctc cctgccagtc ctgagaccca cctggacatg ctccgccacc tgtaccaggg   180
ctgtcaggta gtgcagggca acttggagct tacctacgtg cctgccaatg ccagcctctc   240
attcctgcag gacatccagg aagttcaggg ttacatgctc atcgctcaca accaggtgaa   300
gcgcgtccca ctgcaaaggc tgcgcatcgt gagagggacc cagctctttg aggacaagta   360
tgccctggct gtgctagaca accgagatcc tcaggacaat gtcgccgcct ccaccccagg   420 cagaaccoca gaggggctgc gggagctgca gcttcgaagt ctcacagaga tcctgaaggg   480
```

```
aggagttttg atccgtggga accctcagct ctgctaccag acatggtttt tgtggaagga    540
cgtcttccgc aagaataacc aactggctcc tgtcgatata gacaccaatc gttcccgggc    600
ctgtccacct tgtgccccg cctgcaaaga caatcactgt tggggtgaga gtccggaaga    660
ctgtcagatc ttgactggca ccatctgtac cagtggttgt gcccggtgca agggccggct    720
gcccactgac tgctgccatg agcagtgtgc cgcaggctgc acgggcccca agcattctga    780
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggatcctg    960
cactctggtg tgtcccccga ataaccaaga ggtcacagct gaggacgaaa cacagcgttg   1020
tgagaaatgc agcaagccct gtgctcgagt gtgctatggt ctgggcatgg agcaccttcg   1080
aggggcgagg gccatcacca gtgacaatgt ccaggagttt gatggctgca agaagatctt   1140
tgggagcctg gcatttttgc cggagagctt tgatggggac ccctcctccg gcattgctag   1200
cccgctccag ccagagcagc tccaagtgtt tgagactctg gaagagatca caggttacct   1260
atacatctca gcatggccgg acagcctgcc tgacctcagc gtcttccaga acctgcaagt   1320
aatccgggga cgaattctgc acaatggcgc ctactcgctg accctgcaag gctgggcat   1380 cagctggctg gggctgcgct cactgaggga actgggcagt ggactggccc tcatccacca   1440
taacacccac ctctgcttcg tgcacacggt gccctgggac cagctcttc ggaacccgca    1500 ccaagctctg ctccacactg ccaaccggcc agaggacgag tgtgtgggcg agggcctggc   1560
ctgccaccag ctgtgcgccc gagggcactg ctggggtcca gggcccaccc agtgtgtcaa   1620
ctgcagccag ttccttcggg gccaggagtg cgtggaggaa tgccgagtac tgcaggggct   1680
ccccagggag tatgtgaatg ccaggcactg tttgccgtgc caccctgagt gtcagcccca   1740
gaatggctca gtgacctgtt ttggaccgga ggctgaccag tgtgtggcct gtgcccacta   1800
taaggaccct cccttctgcg tggcccgctg ccccagcggt gtgaaacctg acctctccta   1860
catgcccatc tggaagtttc cagatgagga gggcgcatgc cagccttgcc ccatcaactg   1920
cacccactcc tgtgtggacc tggatgacaa gggctgcccc gccgagcaga gagccagccc   1980
tctgacgtcc atcgtctctg cggtggttgg cattctgctg gtcgtggtct tgggggtggt   2040
ctttgggatc ctcatcaagc gacggcagca agagatccgg aagtaa             2086
```

<210> SEQ ID NO 15
<211> LENGTH: 71
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 15

```
ccggaagtaa ataatcgacg ttcaaataat cgacgttcaa ataatcgacg ttcaaataat    60
cgacgttcaa t                                                         71
```

<210> SEQ ID NO 16
<211> LENGTH: 71
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 16

```
ctagattgaa cgtcgattat ttgaacgtcg attatttgaa cgtcgattat ttgaacgtcg        60
attatttact t                                                              71
```

<210> SEQ ID NO 17
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ccggaagtaa ataatagagc ttcaaataat agagcttcaa ataatagagc ttcaaataat        60
agagcttcaa t                                                              71
```

<210> SEQ ID NO 18
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
ctagattgaa gctctattat ttgaagctct attatttgaa gctctattat ttgaagctct        60
attatttact t                                                              71
```

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
ctaggaagct tgtttaactt gctagct                                             27
```

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
agctagctag caagttaaac aagcttc                                             27
```

<210> SEQ ID NO 21
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
ctagataatc gacgttcaaa taatcgacgt tcaataatc gacgttcaaa taatcgacgt        60
tcaagttt                                                                  68
```

<210> SEQ ID NO 22
<211> LENGTH: 64
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 22
aaacttgaac gtcgattatt tgaacgtcga ttatttgaac gtcgattatt tgaacgtcga     60
ttat                                                                  64

<210> SEQ ID NO 23
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctagataata gagcttcaaa taatagagct tcaaataata gagcttcaaa taatagagct     60
tcaagttt                                                              68

<210> SEQ ID NO 24
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaacttgaag ctctattatt tgaagctcta ttatttgaag ctctattatt tgaagctcta     60
ttat                                                                  64

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
taatacgact cactataggg                                                 20

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggccggttac ccgcgattcc gggggcagg ag                                    32

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccggctagct agcctgtcct tcctgcagga tatcc                                35
```

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccggctagct agcggagggg tcttgatcca gcgga                               35

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccggctagct agcctgccca ctgactgctg ccatg                               35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccggctagct agctgcaccc tcgtctgccc cctgc                               35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccggctagct agcccgctcc agccagagca gctcc                               35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccggctagct agcaacaccc acctctgctt cgtgc                               35

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccggctagct agccccaggg agtatgtgaa tgcca                               35

<210> SEQ ID NO 34

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tagaaggcac agtcgaggct                                                  20

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccggctagct agccgcgatt ccggggggca ggagggcgag gag                        43

<210> SEQ ID NO 36
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctaggcatca tcatcatcat cataatggtc ataccggtga acaaaaactc atctcagaag      60
aggatctgg                                                              69

<210> SEQ ID NO 37
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctagccagat cctcttctga gatgagtttt tgttcaccgg tatgaccatt atgatgatga      60
tgatgatgc                                                              69

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccggctagct agcgctggca ttggcaggca cgtag                                 35

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccggctagct agccaggatc tctgtgagac ttcga                                 35
```

-continued

```
<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccggctagct agcgcccttg caccgggcac aacca                              35

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccggctagct agctcccact tccgtagaca ggtag                              35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccggctagct agcaatgccg gaggaggggt cccca                              35

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ataatcgacg ttcaa                                                    15
```

P185$^{neu}$-ENCODING DNA AND THERAPEUTICAL USES THEREOF

CROSS REFERENCE TO RELATED APPLICATIONS

This application is a division of application Ser. No. 12/874,619 filed on Sep. 2, 2010; which is a division of application Ser. No. 10/574,897 filed on Apr. 6, 2006, now U.S. Pat. No. 7,795,016; which is the 35 U.S.C. 371 national stage of International application PCT/EP2004/011161 filed on Oct. 6, 2004; which claimed priority to Italian application MI2003A001942 filed Oct. 9, 2003. The entire contents of each of the above-identified applications are hereby incorporated by reference.

BACKGROUND OF THE INVENTION

The present invention relates to plasmid vectors containing p185$^{neu}$-encoding sequences and the use thereof in DNA vaccination against tumours. The plasmids according to the invention contain sequences encoding different fragments of human or rat oncoprotein p185$^{neu}$ and are able to induce a humoral or cell-mediated immune response against tumours expressing oncogenes of the ErbB family.

The invention also relates to pharmaceutical compositions containing said plasmids and their use for the prevention or therapy of p185$^{neu}$-expressing tumours.

Protein p185$^{neu}$, one of the most studied tumour antigens, has raised great interest as target for immune therapy against cancer, due to its presence on the cell membrane of some of the most common human carcinomas.

p185$^{neu}$ is a membrane receptor encoded in the rat by proto-oncogene Her-2/neu and belonging to the family of Class I Tyrosine Kinase Receptors (RTKs), which also comprises the Epidermal Growth Factor Receptor EGF-R (ErbB-1) and other receptors related thereto (ErbB-3, ErbB-4). These receptors are involved in cell proliferation and differentiation (Hynes and Stern, 1994 BBA 1198:165) and therefore attract a great biological and clinical interest. The receptor consists of three well distinguished domains: an extracellular, transmembrane and intracytoplasmic domain. p185$^{neu}$ is involved in the complex network of mechanisms of intracellular signal transduction and intracellular communication that regulate proliferation and differentiation processes (Boyle 1992 Curr. Op. Oncol. 4:156). Oncogene neu is named after the chemically-induced rat neuroglioblastoma from which it was first isolated. This activated neu form has a single point mutation that results in the replacement of "A" with "T" and in the consequent substitution of the Valine residue at position 664 of p185$^{neu}$ with a glutamic acid residue (Val664Glu) (Bargmann et al. 1986, Cell 45:649).

Also the human neu homologous, ErbB-2, has been isolated and characterised and it has been demonstrated that both rat HER2/neu receptor and human ErbB2 have a significant homology with EGFR (Coussens et al. 1985, Sciente 230: 1132; Yamamoto et al. 1986, Nature 319:230). While a genetic mutation in the rat sequence is the cause of constitutive receptor activation through dimerization, in ErbB-2 positive human tumours an aberrant expression of the oncogene is observed (Di Marco et al. 1990, Mol. Cell. Biol. 10: 3247; Klapper et al., 2000, Adv Cancer Res, 77:25), even though, in rare cases, activating point mutations and abnormal splicing mechanisms have been found (Kwong et al., 1998, Mol Carcinog, 23:62; Xie et al., 2000, J Natl Cancer Inst, 92:412). The overall effect is similar: gene amplification and increase in the transcription level determine an excess of p185$^{neu}$ membrane receptor, with consequent increase of active dimers intracellularly transducing growth signals in a ligand-independent manner. The crystal structure of human and rat p185$^{neu}$ extracellular region recently reported shows that this protein is characterised by a rigid conformation that allows to interact with other ErbB receptors, without directly binding any ligands, and trigger the proliferation signal transduction (Cho H S et al. 2003, Nature 421:756).

Under normal circumstances, human p185$^{neu}$ is involved in organogenesis and epithelial growth; it is expressed at high levels during placenta formation and fetal development, whereas it is present at very low levels in adult tissues (Press et al. 1990, Oncogene 5:953).

Several studies have demonstrated that human p185$^{neu}$ overexpression is associated to the neoplastic process and to the level of tumor aggression. The overexpression of p185$^{neu}$ has been described in lung (Kern et al. 1986, Cancer Res. 50:5184), colon (Cohen et al. 1989, Oncogene 4:81), ovary (Slamon et al. 1989, Science 244:707) adenocarcinomas and in a high number of human mammary carcinomas (Slamon et al. 1989, Science 244:707; Jardines et al. 1993, Pathobiology 61:268).

The fundamental properties that make p185$^{neu}$ an optimal target for plasmid vaccination are: a) its direct involvement in cell growth and carcinogenesis, therefore clone variants that, due to tumour genetic instability, lose the expression of this antigen also lose their tumorigenicity; b) its expression on the plasmatic membrane, which makes it recognizable by antibodies even in tumour cells that lose the expression of the major histocompatibility system (Lollini P. and Forni G. 2003, Trends Immunol. 24: 62).

Studies carried out on mice transgenic for the activated rat oncogene Her-2/neu (which spontaneously develop p185$^{neu}$ positive mammary tumours) and on murine models using p185$^{neu}$ positive transplantable tumour lines, have demonstrated the possibility to prevent and cure preneoplastic lesions. As regards in particular the prevention of mammary tumours in mice transgenic for rat activated Her-2/neu, we have demonstrated that the plasmid coding for the extracellular and transmembrane domains of rat p185$^{neu}$ is able to induce an in vivo protection more effective than the plasmid encoding for the full-length rat p185$^{neu}$ or for the extracellular domain only (secreted antigen) (Amici A. et al. 2000, Gene Ther., 7: 703; Rovero S. et al. 2000, J. of Immunol., 165: 5133). Similar results have been reported by Chen et al. (1998, Cancer Res 58:1965). Other authors have demonstrated that plasmids encoding for p185$^{neu}$—either unvaried or mutated so as to eliminate its tyrosine-kinase activity—are effective in preventing the onset of tumours following to p185$^{neu}$-positive cells inoculum (Wei W Z et al. 1999, Int. J. Cancer 81: 748). Moreover, plasmids devoid of the signal responsible for the processing through the endoplasmic reticulum (leader), which determines cytoplasmic localization of p185$^{neu}$ antigen, proved equally effective. The protection induced by different plasmids was mainly mediated by a humoral immune response in the case of membrane expression of p185$^{neu}$ and by a T-lymphocyte-mediated immune-response in the case of cytoplasmic localization (Pilon S A et al. 2001, J. of Immunol. 167: 3201). However, combined vaccination with plasmids inducing p185$^{neu}$ overexpression in both the cytoplasm and the membrane was more effective in protecting against tumour growth (Piechocki M P et al. 2001, J. Immunol. 167: 3367).

Thus, the balance between different immune response mechanisms might be particularly important (Reilly et al., 2001, Cancer Res. 61: 880). Moreover, it has been observed that the vaccination with plasmids encoding for extracellular and transmembrane domains of rat p185$^{neu}$ is able to eradicate tumour masses with 2 mm diameter, upon inolculum of cells overexpressing p185$^{neu}$, through a number of different effector mechanisms of the immune system (T helper and T killer cells, antibodies, macrophages, neutrophiles, natural killer cells, Fc receptors, gamma interferon and perforins), which cooperate to tumor rejection (Curcio C. et al. 2003, J. Clin. Invest. 111: 1161).

DESCRIPTION OF THE INVENTION

Various constructs encoding the human or human/rat chimeric p185 protein have been inserted in plasmid vectors and used in immunization experiments aimed at preventing tumour progression. For plasmid construction, fragments of the human p185$^{neu}$ protein containing the transmembrane domain and portions of the extracellular domain of decreasing length have been prepared from ErbB2 oncogene sequence, or portions thereof have been replaced with homologous sequences from the rat Her-2/neu cDNA so as to create chimeric plasmids.

The plasmids thereby obtained have been evaluated in vaccination experiments in mice inoculated with tumour cells overexpressing human p185$^{neu}$. Plasmids containing truncated forms of p185$^{neu}$ induced an antitumor reactivity mediated by killer and helper T lymphocytes, while chimeric plasmids induced an antibody response against both human and rat p185$^{neu}$.

Based on the results of in vivo experiments, the plasmids containing p185$^{neu}$ sequences able to induce a strong immune response of both cellular and humoral type have been selected. These plasmids, object of the present invention, contain a sequence encoding a p185$^{neu}$ fragment selected from the group consisting of SEQ ID N. 1-14 (human and rat p185$^{neu}$ reference sequences are available at Gene Bank accession numbers M11730 and X03362, respectively).

According to the invention, p185$^{neu}$ encoding sequences can be inserted in any plasmid vectors suitable for human administration. Besides the encoding sequences, the plasmids can contain functional elements for transcription control, in particular a promoter placed upstream of the encoding sequence, preferably the CMV promoter, start and stop transcription elements, selection markers, such as ampicillin or kanamicin resistance genes, CpG motifs, a polyadenilation site or transcription activators. Transcription control elements should be compatible with the use of the vector in humans. In a preferred embodiment, the plasmids of the invention contain at least 4 CpG motifs, preferably at least 8, up to a maximum of 80. The CpG motifs (ATAATCGACGTTCAA) (SEQ ID NO: 43) of bacterial origin induce macrophages to secret IL-12, which in turn induce IFN gamma secretion by natural killer cells, thus activating a T helper lymphocyte-mediated response (Chu R. S. et al. 1997, J. Exp. Med., 186: 1623). Therefore, the insertion of CpG motifs in plasmid sequences enhances the immune response.

In a further embodiment, the invention provides a pharmaceutical composition containing one or more different plasmids as defined above in association with pharmaceutically acceptable vehicles and excipients. The pharmaceutical compositions, in a form suitable for parenteral administration, preferably in the form of injectable solution, are conveniently used for DNA vaccination. Principles and methods for DNA vaccination are known to the skilled in the art and are disclosed, for example, in Liu M A 2003; J Int Med 253: 402.

In another embodiment, the invention provides a combined preparation containing at least two, preferably at least four, more preferably at least eight different plasmids for simultaneous, sequential or separate administration to a subject or patient.

Plasmids, compositions and preparations according to the invention are used in preventive or therapeutical treatment of subjects at risk of developing p185$^{neu}$-positive tumours, or patients with primary tumours, metastasis or relapses of p185$^{neu}$-positive tumours. Prevention can be primary, when the tumour is not manifest, secondary, when the tumour is in the initial phases as a preneoplastic lesion, o tertiary, in the case of tumour relapse or metastatic process. Tumours that can benefit from treatment with the plasmids of the invention are those of epithelial origin, in particular pulmonary, ovary and mammary adenocarcinomas and, more generally, tumours expressing the p185$^{neu}$ protein.

DETAILED DESCRIPTION OF THE INVENTION

Figure 1:
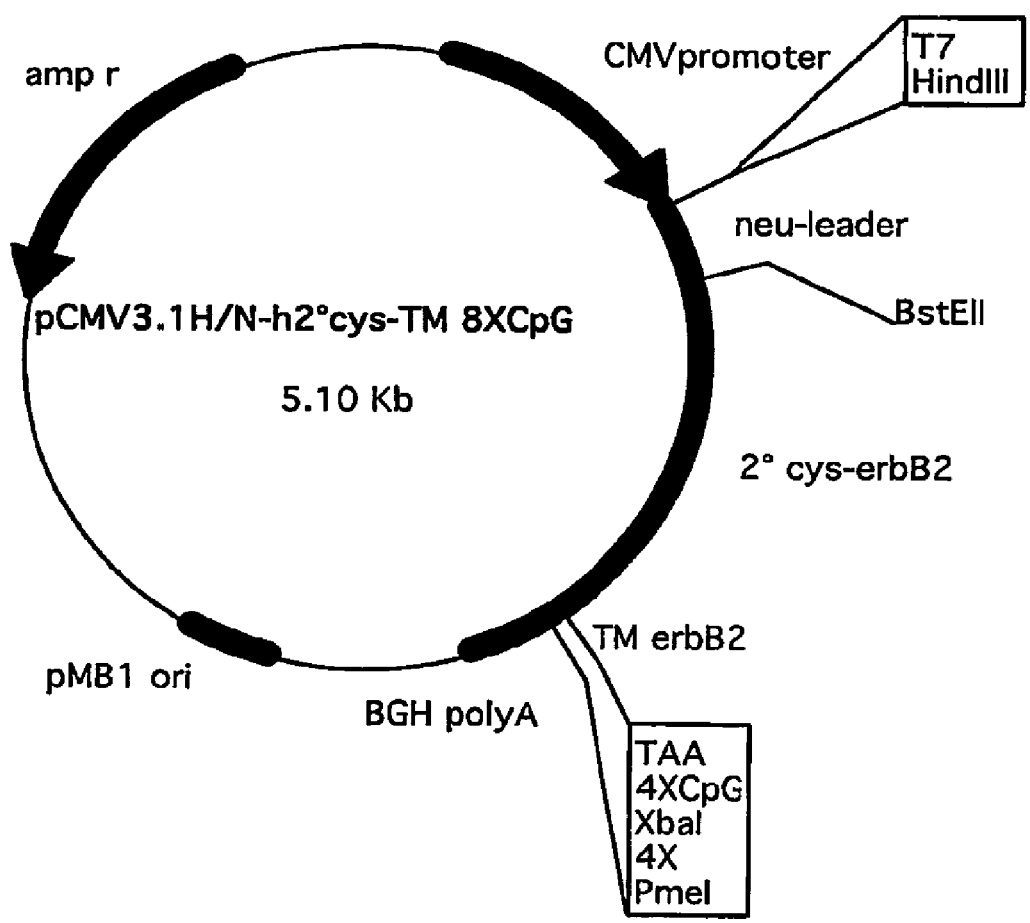
FIG. 1 illustrates the construction of a plasmid containing the sequence of the second cysteine domain and transmembrane domain of human p185neu.

Construction of the Plasmid Backbone of pCMV3.1

To construct plasmids encoding human p185$^{neu}$ fragments and chimeric plasmids, the pCMV3.1 plasmidic backbone was used. Fragments deriving from human proto-oncogene ErbB-2 cDNA and from rat proto-oncogene Her-2/neu cDNA have been inserted in pCMV3.1 (Invitrogen, Milano, Italia) by removing with restriction enzymes DraIII (nt1531) e BsmI (nt3189) a fragment of 1658 bp containing the replication origin f1, the replication origin and the early SV40 promoter, the gene encoding for neomicine resistance and SV40 polyadenylation signal. The resulting modified plasmid (pCMV3.1) present some advantages compared to native pcDNA3.1. In fact, the size reduction to 3900 bp and the removal of irrelevant sequences contribute to increase transfection efficacy in vivo.

Construction of Plasmid pCMV3.1erbB2

Human ErbB2 cDNA, obtained from plasmid pSVerbB2, has been inserted in the multiple cloning site of pCMV3.1 at restriction sites HindIII and XbaI. This plasmid is used for the construction of plasmids expressing truncated p185$^{neu}$ and chimeric plasmids.

Construction of Plasmids Containing the Sequence 4XCpG: pCMV3.1hECD-TM-4 CpG and pCMV3.1hECD-TM-4-noCpG After removal of the sequence encoding the intracytoplasmic domain from plasmid pCMV3.1-erbB2, two plasmids coding for proto-oncogene ErbB2 extracellular and transmembrane regions were prepared. The procedure comprised first the restriction analysis to identify the unique sites present in the nucleotide sequence of ErbB2 cDNA. A unique site recognized by enzyme AccIII (nt 2195) about 20 bp downstream of the end of the transmembrane domain was identified.

The cytoplasmic domain was removed using the enzyme AccIII present as unique restriction site and enzyme XbaI. To re-insert at the 3' end of the DNA of the ErbB2 ECD-TM the nucleotide triplet TAA, recognized as translation stop signal, we used two synthetic sequences consisting of two sense (oligonucleotide #1, #3) and antisense (oligonucleotide #2, #4) oligonucleotides having the restrictions sites AccIII and XbaI at their ends. In these synthetic sequences there are also four repeated sequences CpG and noCpG. The latter is used as negative control. These two new plasmids have been named pCMV3.1hECD-TM-4 CpG and pCMV3.1hECD-TM-4-noCpG.

Construction of the Plasmids Containing the Sequence 8XCpG: pCMV3.1H/NhECD-TM-8 CpG and pCMV3.1H/NhECD-TM-8noCpG To add further aspecific immune stimuli we constructed a new plasmid backbone containing 4 immune-stimulating CpC sequences, called pCMV3.1 H/N-4 CpG. For this purpose we modified pCMV3.1 so as to remove one of the two restriction sites for the enzyme PmeI and invert the restriction sites for HindIII and NneI present on the multiple cloning site by means of a synthetic sequence consisting of two sense (oligonucleotide #5) and antisense (oligonucleotide #6) oligonucleotides. In this new plasmid, named pCMV3.1 H/N, two synthetic sequences have been inserted, consisting of two sense (oligonucleotide #7, #9) and antisense nucleotides (oligonucleotide #8, #10), containing four repeats for the CpG and noCpG sequences in the unique restriction sites XbaI and PmeI, thus obtaining pCMV3.1 H/N-4 CpG and 4noCpG. Thereafter, DNA fragments hECD-TM-4 CpG and hECD-TM-4-noCpG have been inserted in pCMV3.1 H/N-4 CpG and in pCMV3.1 H/N-4-noCpG respectively, thus obtaining two new plasmids called pCMV3.1H/N-hECD-TM-8 CpG and pCMV3.1H/N-hECD-TM-8noCpG.

Construction of the Plasmid Containing the Sequence of the Second Cystein Domain and Transmembrane Domain of Human p185$^{neu}$: pCMV3.1H/Nh2°cysECD-TM-8 CpG Human p185$^{neu}$ extracellular domain is characterised by two regions rich in cysteines, known as $1^{st}$ and $2^{nd}$ cystein sub-domain ($1^{st}$ cys and $2^{nd}$ cys). Unlike the rat cDNA sequence containing only one site BstEII (nt1250) in the extracellular domain, located in the nucleotide region that separates $1^{st}$ cys from $2^{nd}$ cys, the cDNA sequence of the extracellular domain of ErbB2 has two restriction sites for BstEII: in addition to the site in the same position as that of rat (nt1372), a further BstEII site (nt963) is present in the portion encoding the $1^{st}$ cys of the extracellular domain. Digesting plasmid pCMV3.1H/NhECD-TM-8 CpG with HindIII and BstEII, a DNA fragment consisting of the 2nd cys from the extracellular domain, the transmembrane domain, the sequence 8 CpG and the plasmid pCMV3.1H/N was obtained. Then the signal for rat p185neu secretion through the endoplasmic reticulum was inserted by enzymatic DNA amplification (PCR reaction) using a sense oligonucleotide consisting of the primer T7 (oligonucleotide #11) which recognizes the T7 RNA polymerase, present at the beginning of the pCMV3.1H/N multiple cloning site, and an antisense oligonucleotide (oligonucleotide #12) having the BstEII site at its end. After purification, enzymatic digestion of the amplified fragment with restriction enzymes HindIII and BstEII and subsequent cloning, pCMV3.1H/Nh2°cys-TM-8 CpG (FIG. 1) has been obtained. (FIG. 1). This plasmid was used in vaccination experiments, to have it compared with pCMV3.1 H/NhECD-TM-8 CpG. Thereafter, a chimeric cDNA encoding for the fusion protein between $2^{nd}$ cys and transmembrane domain (nt 1372-nt 2204) of the human sequence and $1^{st}$ cys (nt 1-nt 1250) of the rat sequence has been prepared. The reconstitution of the entire protein sequence by the fusion of portions deriving from rat and human cDNAs, respectively, allows to increase the immune response.

Figure 2:
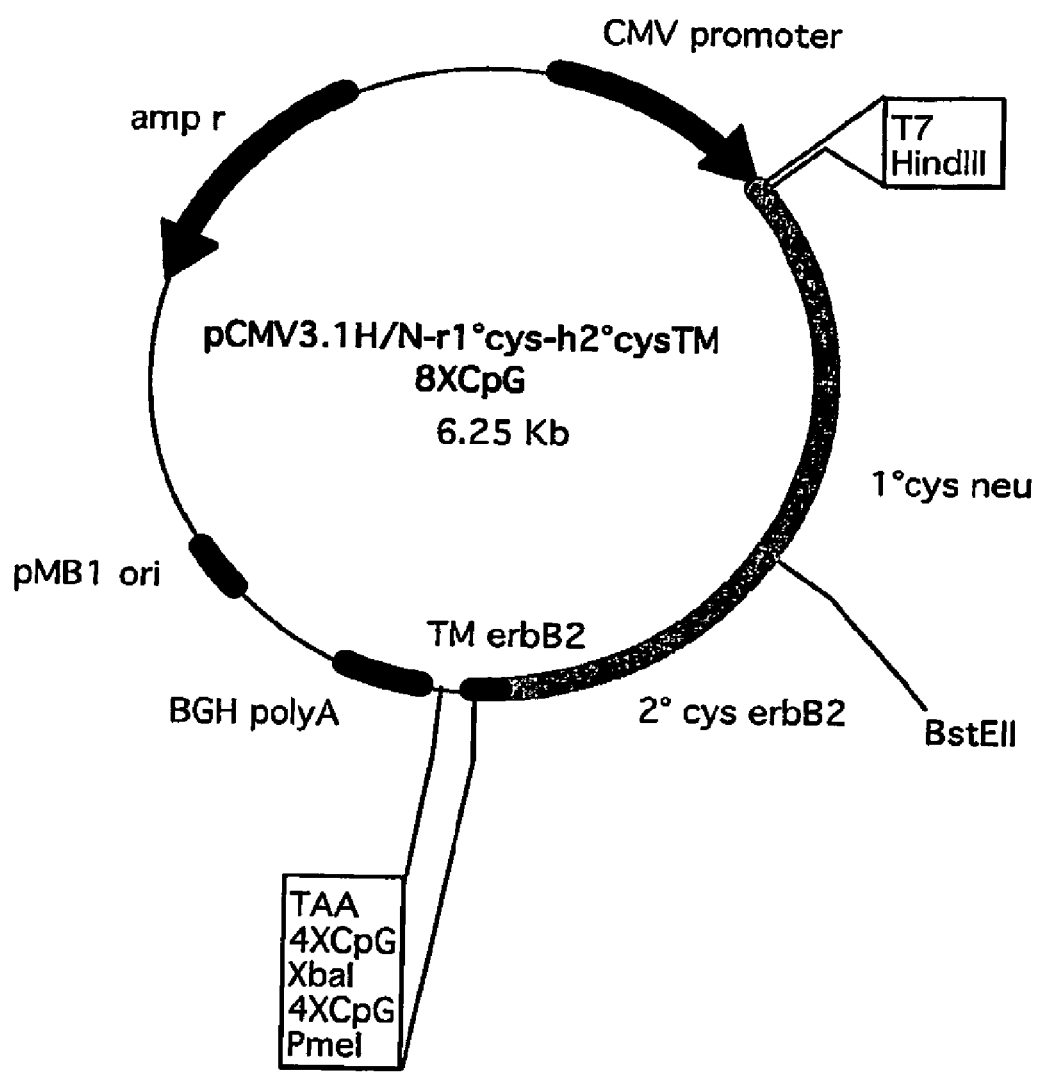
FIG. 2 illustrates the construction of a chimeric plasmid containing the sequence of the first cysteine domain of rat p185neu and of the second cysteine domain and transmembrane domain of human (nt 1-1250).

Construction of the Chimeric Plasmid Containing the Sequence of the First Cystein Domain of Rat p185neu and of the Second Cystein Domain and Transmembrane Domain of Human (Nt 1-Nt 1250): pCMV3.1H/N-r1°cys-h2°cysTM-8 CpG Unlike the rat cDNA sequence containing only a BstEII (nt1250) site in the extracellular domain located in the nucleotide region that separates the first and the second region rich in cysteins, the cDNA sequence of the extracellular domain of Erb2 has two restriction sites for BstEII: one in position 1372 (nt), as in the rat sequence, and the other in position 963 (nt), i.e. in the sequence portion encoding for the $1^{st}$ cys of the extracellular domain. The presence of the BstEII site in the same position both in the rat cDNA domain (1250nt) and in the human cDNA (1372nt) allowed the construction of a plasmid able to encode a fusion product between rat $1^{st}$ cys and human $2^{nd}$ cys. In fact, digesting pCMV3.1H/N-h2°cysTM-8 CpG with restriction enzymes HindIII and BstEII allowed to replace the DNA fragment encoding for rat p185$^{neu}$ secretion signal with the nucleotide sequence encoding for rat 1st cys obtained through digestion of pCMV3.1rECD-TM-4CpG with the same enzymes. The product of plasmid pCMV3.1H/N-r1°cys-h2°cysTM-8 CpG (FIG. 2) consists of a portion of 412 aa of rat p185neu and a portion of 274 aa of human p185$^{neu}$. This new plasmid, pCMV3.1H/Nr1°cys-h2°cysTM-8 CpG has been used in vaccination experiments using pCMV3.1H/N-hECD-TM-8 CpG as comparative term. Surprisingly, the plasmid coding for the chimeric protein induces in mice a complete protection against tumours expressing human p185$^{neu}$ (Table). This protection is similar to that induced by pCMV3.1H/N-hECD-TM-8 CpG. Moreover, analysis of the sera of mice vaccinated with both plasmids has evidenced a similar antibody titer towards human p185$^{neu}$.

Plasmids Able to Encode Decreasing Fragments of the Extracellular and Transmembrane Domain of Human p185 neu Construction of seven plasmids that encode decreasing fragments of the extracellular and transmembrane domain of human p185$^{neu}$, namely: pCMV3.1H/NhECD1-TM-8 CpG (−70 aa), pCMV3.1H/NhECD2-TM-8 CpG (−150 aa), pCMV3.1H/NhECD3-TM-8 CpG (−230 aa), pCMV3.1H/NhECD4-TM-8 CpG (−310 aa), pCMV3.1H/NhECD5-TM-8 CpG (−390 aa), pCMV3.1H/NhECD6-TM-8 CpG (−470 aa) and pCMV3.1H/NhECD7-TM-8 CpG (−550 aa).

The fragment encoded by the first of these fragments is 70 aa (deletion of 360 bp) shorter. All the others are gradually 80 aa shorter (deletions of 240 bp).

Figure 3:
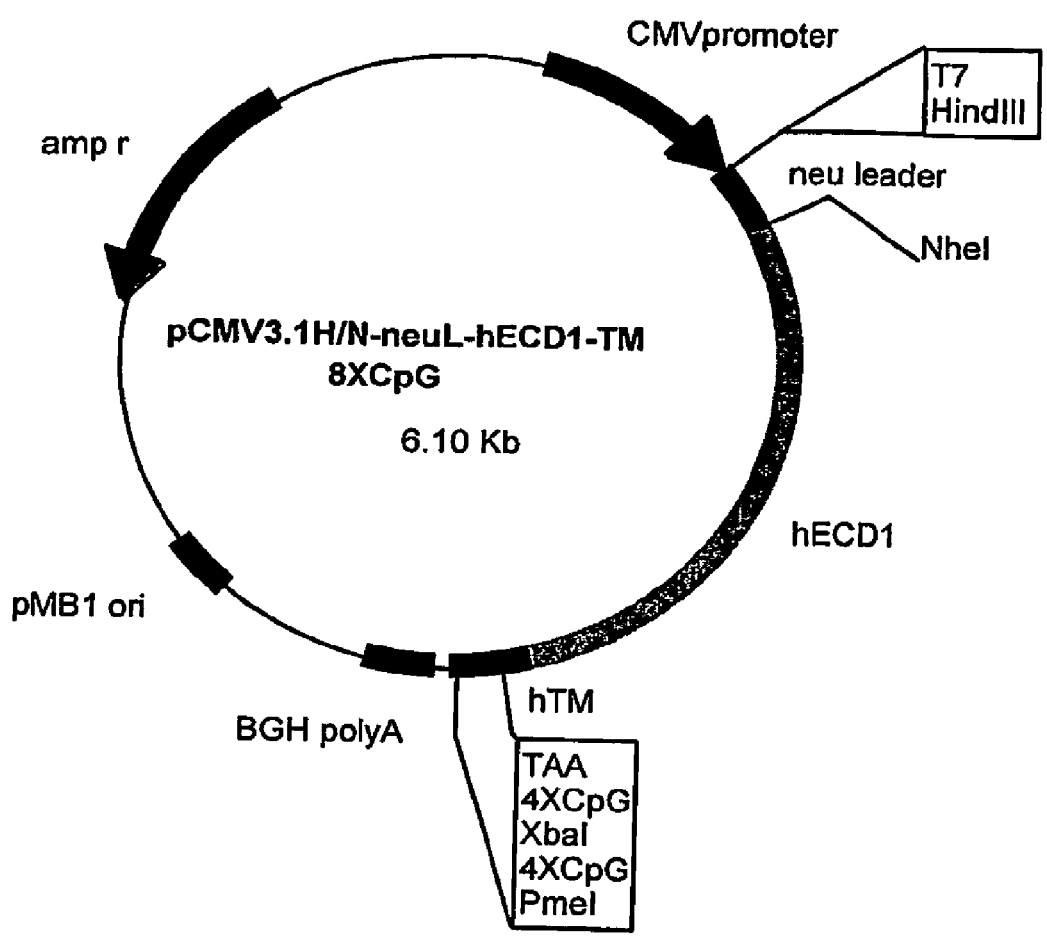
FIGS. 3-9 illustrate the construction of seven plasmids encoding decreasing fragments of the extracellular domain of human p185neu.
Figure 4:
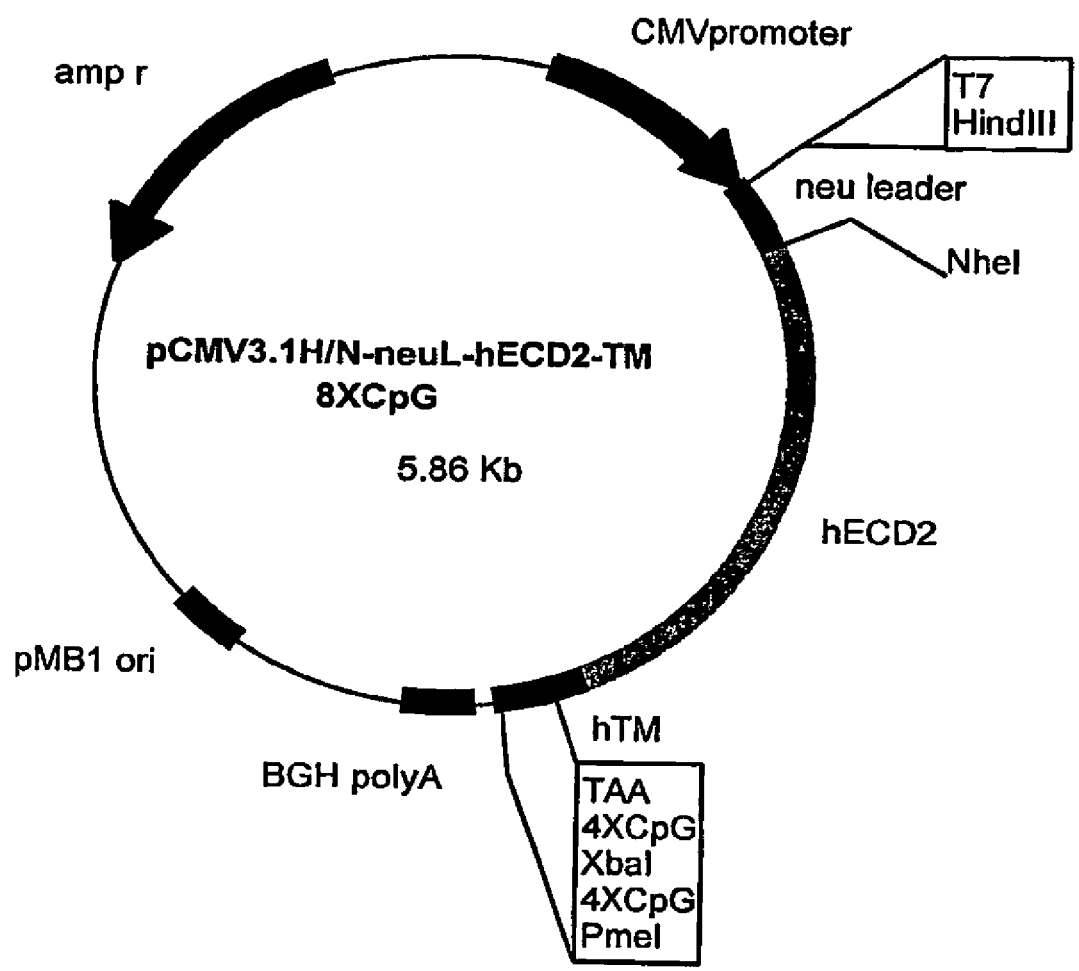
Figure 5:
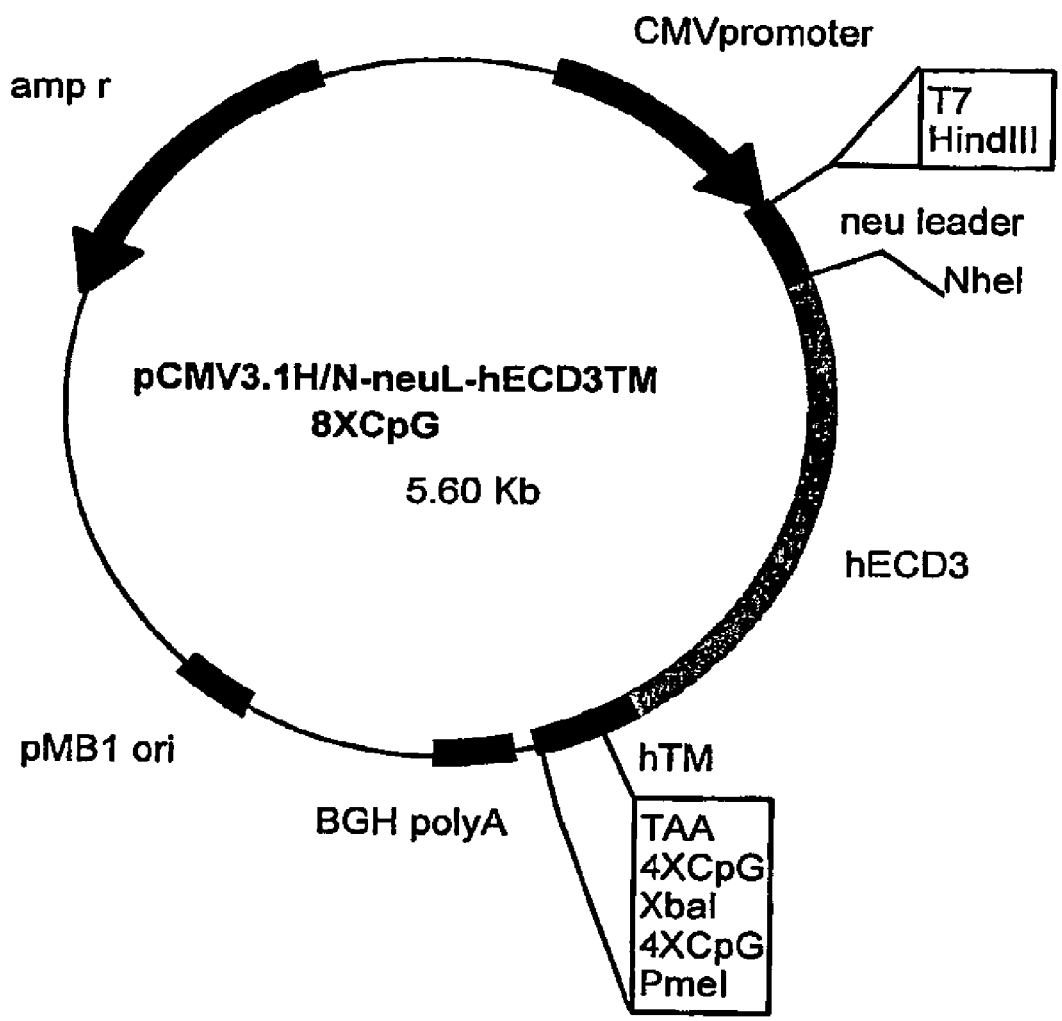
Figure 6:
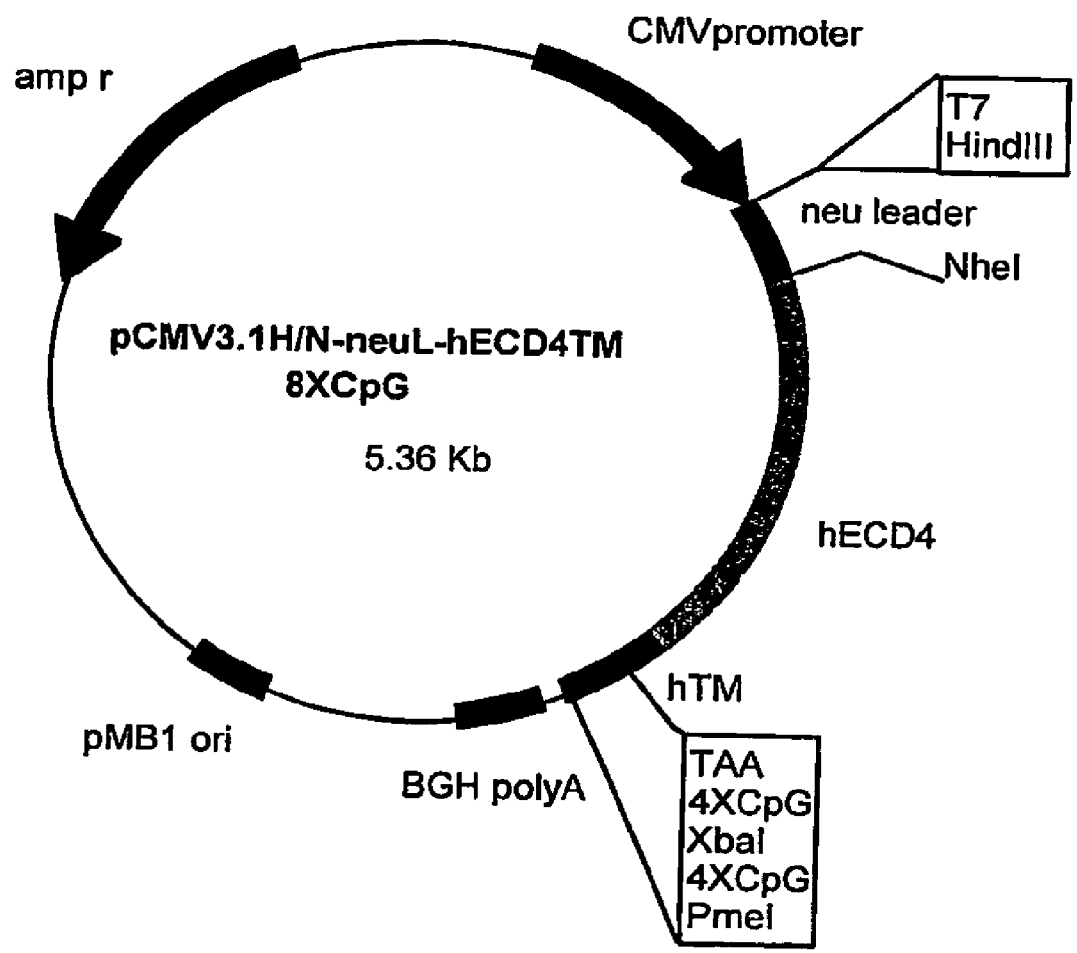
Figure 7:
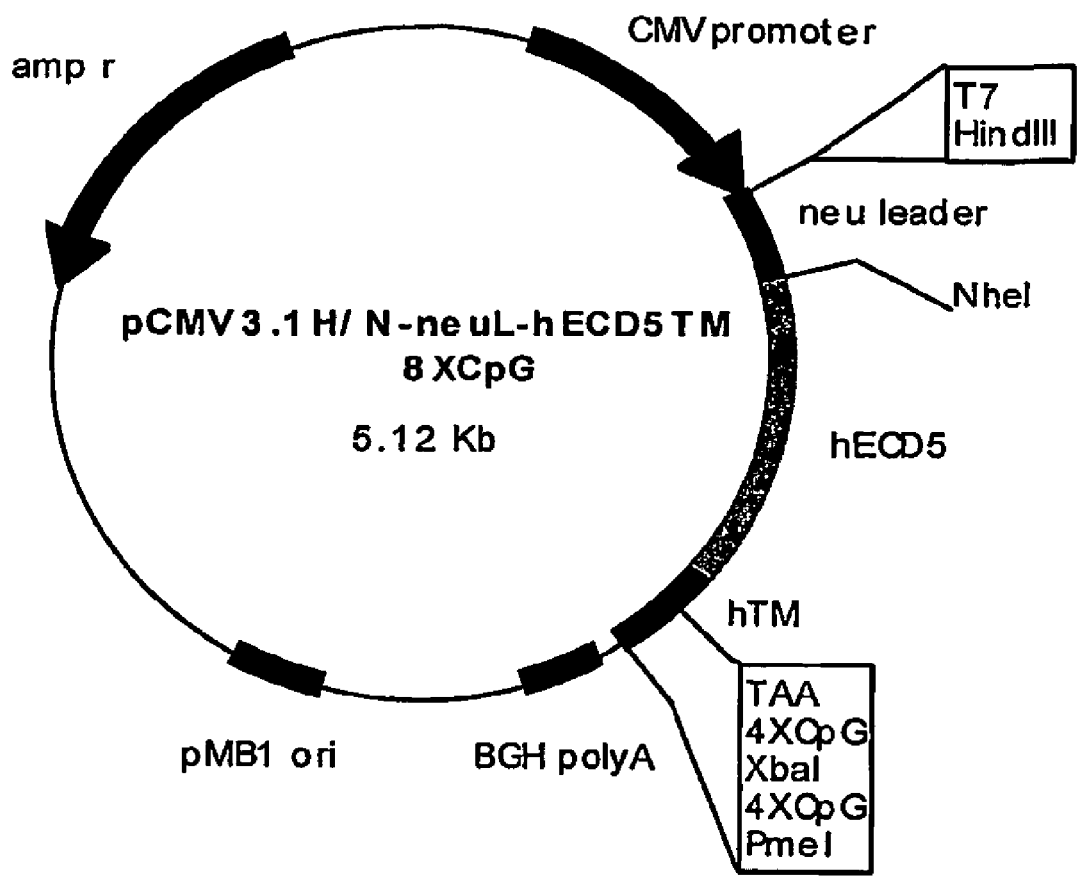
Figure 8:
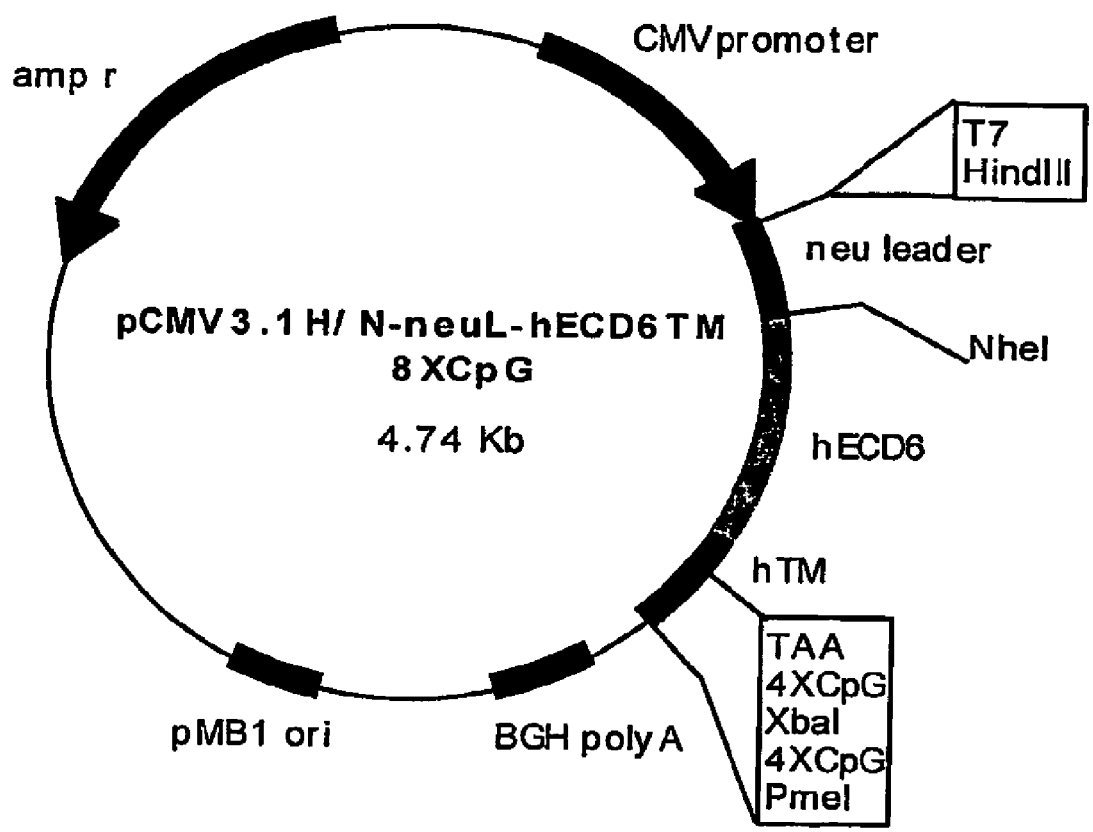
Figure 9:
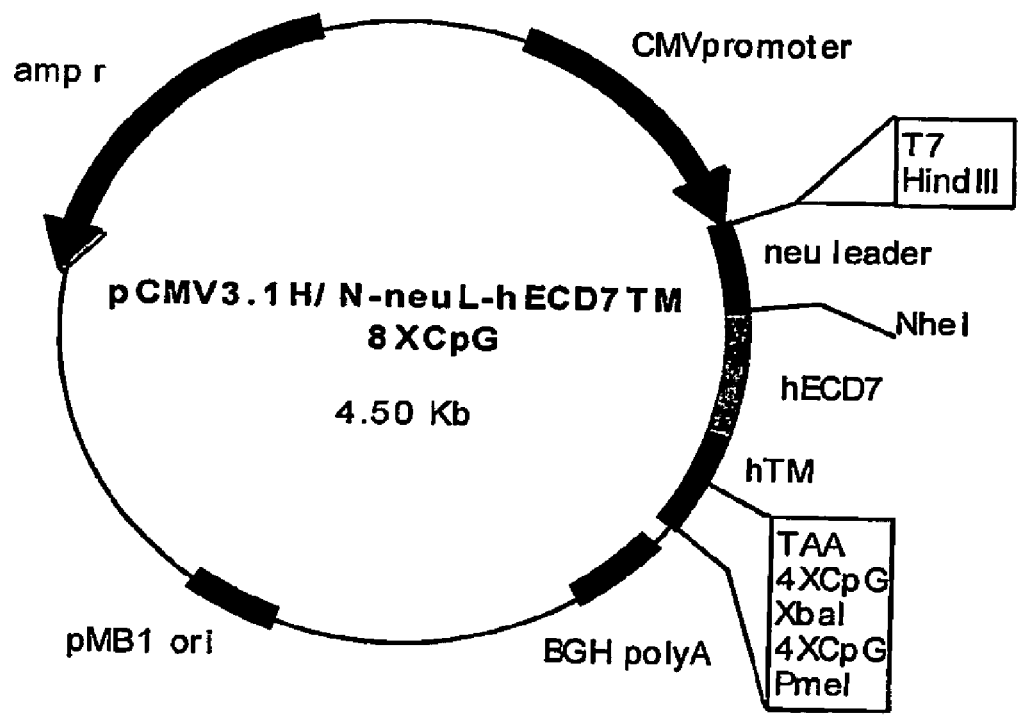

These fragments have been obtained by DNA enzymatic amplification, using seven different sense oligonucleotides with NheI restriction site (oligonucleotides #13-#19) at its end and an antisense oligonucleotide (oligonucleotide #20) able to recognise the site called "pcDNA3.1/BGH Reverse priming site" (830-850 nt) present at the 3' end of the polylinker of pCMV3.1. Further to enzymatic digestion with restriction enzymes NheI and PmeI, amplification products have been cloned in pCMV3.1H/N-neu leader, previously obtained inserting the secretion signal to the endoplasmic reticulum of rat p185$^{neu}$ in restriction sites. The DNA fragment of rat p185$^{neu}$ secretion signal has been obtained by enzymatic DNA amplification using primer T7 (oligonucleotide #11) as sense nucleotide and an antisense nucleotide (oligonucleotide #21) with NheI site at its end. The amplified fragment after purification and restriction digestions with HindIII and NheI has been cloned in plasmid pCMV3.1H/N, digested with the same enzymes, thus obtaining the pCMV3.1H/N-neu leader. Membrane expression of the different truncated forms of human p185$^{neu}$ is expected in view of the presence of the secretion signal to the endoplasmic reticulum of rat p185$^{neu}$. The plasmids encoding the truncated forms pCMV3.1H/NhECD1-TM-8 CpG (FIG. 3), pCMV3.1H/NhECD2-TM-8 CpG (FIG. 4), pCMV3.1H/NhECD3-TM-8 CpG (FIG. 5), pCMV3.1H/NhECD4-TM-8 CpG (FIG. 6) as well as the control plasmid pCMV3.1H/NhECD-TM-8 CpG, protect 100% of the vaccined mice against a lethal inoculum of tumour cells expressing human p185$^{neu}$ (Table). Plasmid pCMV3.1H/NhECD5-TM-8 CpG (FIG. 7) protects 60% of the animals (Table), while plasmids pCMV3.1H/NhECD6-TM-8 CpG and pCMV3.1H/NhECD7-TM-8 CpG (FIG. 8, 9), do not have protective effect against a lethal inoculum of tumour cells expressing human p185$^{neu}$ (Table). The protein products expressed by the different plasmids are not secreted through the endoplasmic retuculum. The absence of consensus sequences necessary for glycosilation and for their processing through the endoplasmic reticulum, or conformational changes due to deletion of aminoacids at the —NH$_2$ terminus, could explain the absence of protein products in the membrane. Therefore, to further verify if the various truncated forms of the extracellular and transmembrane domain of human p185$^{neu}$ were correctly expressed, new plasmids coding for fusion proteins characterized by epitope myc at the —NH$_2$ terminus were generated. These recombinant proteins are recognized by an anti-myc monoclonal antibody, therefore it is possible to analyse their expression and localisation by confocal microscopy.

First a new plasmid coding for the secretion signal to the rat endoplasmic reticulum (neu leader) and for the myc epitope has been created. Cloning has been carried out using a synthetic sequence consisting of a sense (oligonucleotide #22) and antisense (oligonucleotide #23) having at both ends the NheI site. The NheI site in the 5' position was mutated so that, once correctly ligated, it was not recognized by the enzyme. We thus obtained the pCMV3.1H/Nneuleader-myc epitope. With this plasmid, the sequences encoding human p185$^{neu}$ truncated forms have been cloned in the restriction sites NheI and PmeI. Then, 3T3 NIH fibroblasts have been transfected in vitro with plasmids using lipofectamine 2000 (Invitrogen, Milan, Italy). After 48 hours the transfected cells have been analysed with confocal microscopy, using a FITC-conjugated anti-myc monoclonal antibody (Sigma-Aldrich Srl, Milan, Italy). It has been thus demonstrated that all the pasmids-encoded truncated forms are located in the cytoplasm. 3T3 NIH fibroblasts have been transfected in parallel with plasmid pCMV3.1H/NhECD-TM-8 CpG and analysed with confocal microscopy using c-erbB2/c-neu Ab-3 monoclonal antibody (Oncogene, Boston, Mass.) as primary antibody and a FITC-conjugated anti-mouse secondary antibody (PharMigen, San Diego, Calif.). It was thus observed that human ECD-TM is expressed in the membrane. The results obtained using the first four plasmids described previously (pCMV3.1H/NhECD1-TM-8 CpG, pCMV3.1H/NhECD2-TM-8 CpG, pCMV3.1H/NhECD3-TM-8 CpG, pCMV3.1H/NhECD4-TM-8 CpG), demonstrate that a cellular response is sufficient for antitumour prevention. However, it is known that contemporaneous activation of the cellular and humoral response is necessary for a more effective therapy (Rielly et al., 2001, Cancer Res 61:880). As already described in the previous paragraph, the chimeric protein encoded by plasmid pCMV3.1H/N-r1°cys-h2°cysTM-8 CpG is able to protect 100% of the vaccined animals and is able to induce a strong humoral response in the mice.

Chimeric Plasmids Able to Encode for Five Different Man-Rat Chimeric p185$^{neu}$ For the construction of plasmids coding for chimeric proteins, we selected pCMV3.1H/NhECD1-TM-8 CpG, pCMV3.1H/NhECD2-TM-8 CpG, pCMV3.1H/NhECD3-TM-8 CpG and pCMV3.1H/NhECD4-TM-8 CpG. These four plasmids protect 100% of the vaccinated mice against a lethal inoculum of tumour cells expressing human p185$^{neu}$. Also plasmid pCMV3.1H/NhECD5-TM-8 CpG has been selected, even if it protects only 60% of the vaccinated mice, because the encoded protein differs only by 17 aa from that encoded by pCMV3.1H/Nh2°cysECD-TM-8 CpG (275 aa), which protects 20% of the vaccinated mice. We can hypothesize that the peptide sequence of 17 aa corresponds to an important epitope for the induction of an effective immune response.

DNA fragments encoding for rat p185$^{neu}$ portions have been obtained by DNA enzymatic amplification. To amplify these cDNA fragments six oligonucleotides having all the same orientation, namely that of T7 primer (oligonucleotide #11), have been used, while the five antisense have been designed to recognize rat cDNA in the proper positions and have the restriction site for NheI at their ends (oligonucleotides #24-#28). After purification and digestion with restriction enzymes HindIII and NheI, the amplified fragments have been inserted in the corresponding plasmids (pCMV3.1H/NhECD1-TM-8 CpG, pCMV3.1H/NhECD2-TM-8 CpG, pCMV3.1H/NhECD3-TM-8 CpG, pCMV3.1H/NhECD4-TM-8 CpG pCMV3.1H/NhECD5-TM-8 CpG) and digested with the same restriction enzymes. In this way we obtained five new plasmids able to code for chimeric proteins of 689 aa, of which 2 (Val-Ser) belong to restriction site NheI used for the conjuction between rat and human DNA. The presence of these two aa renders both human and rat portions heterolytic.

Figure 10:
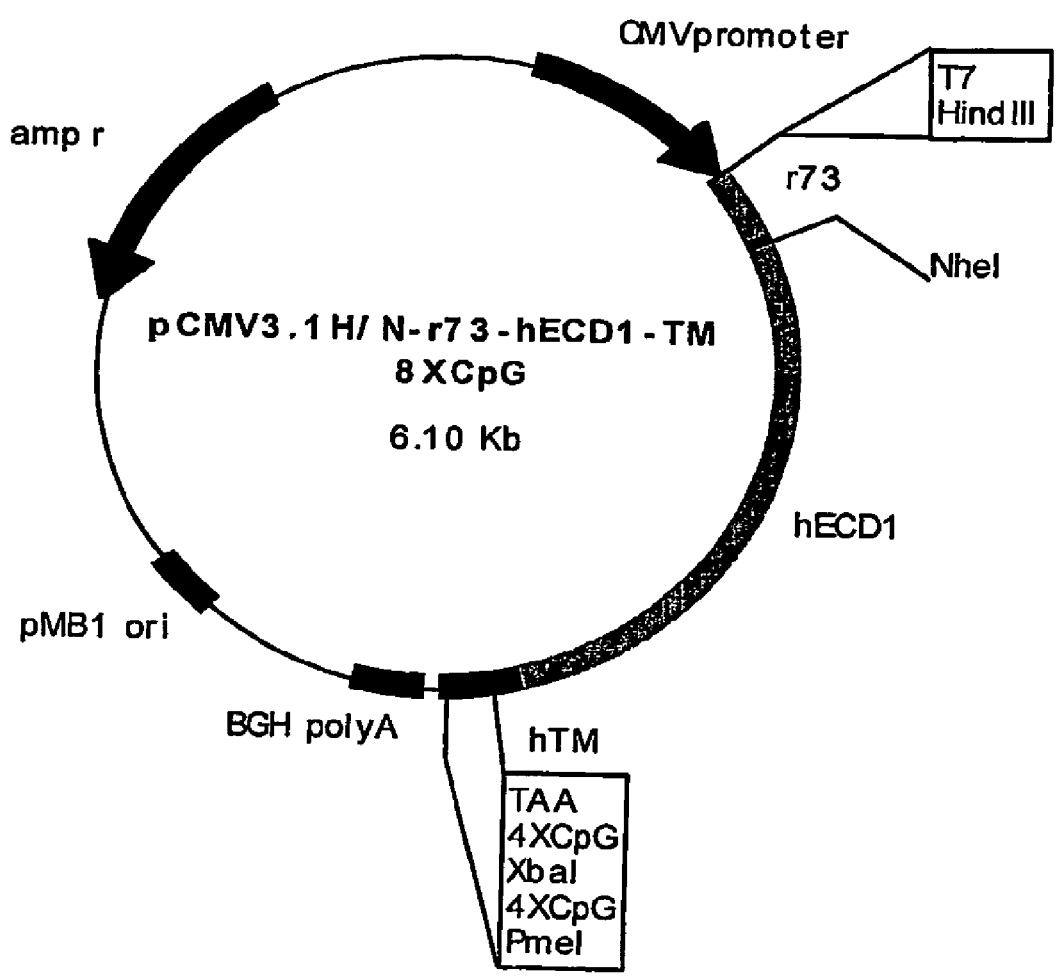
FIGS. 10-14 illustrate the construction of five plasmids encoding for different man-rat chimeric p185neu.
Figure 11:
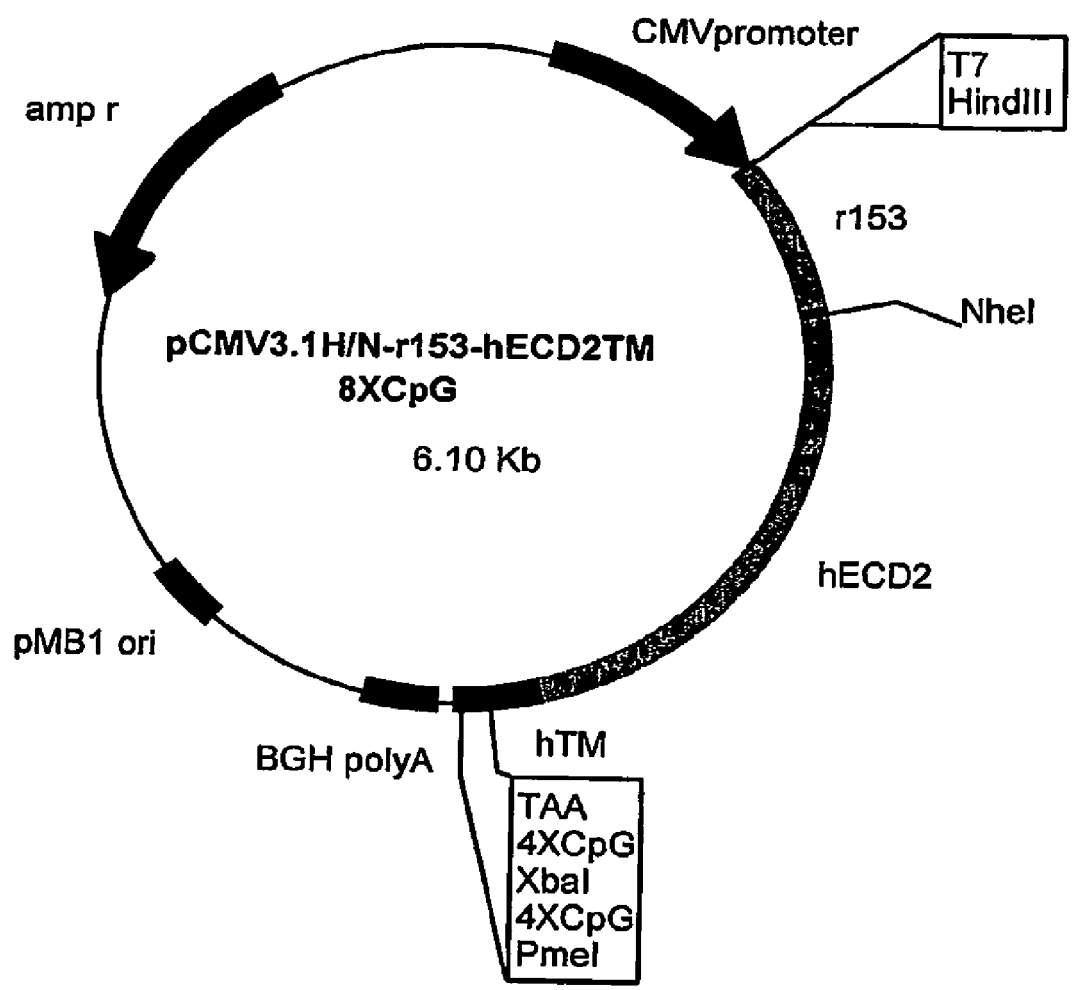
Figure 12:
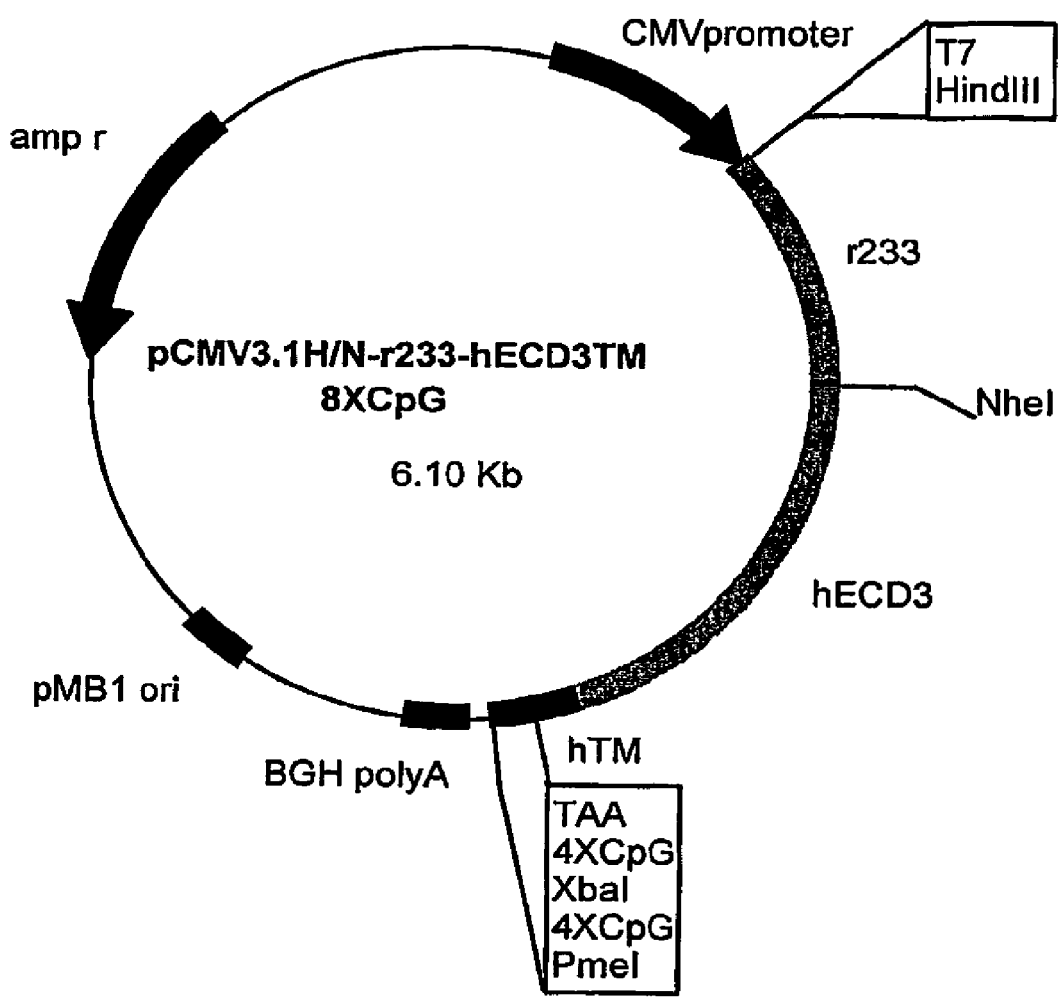
Figure 13:
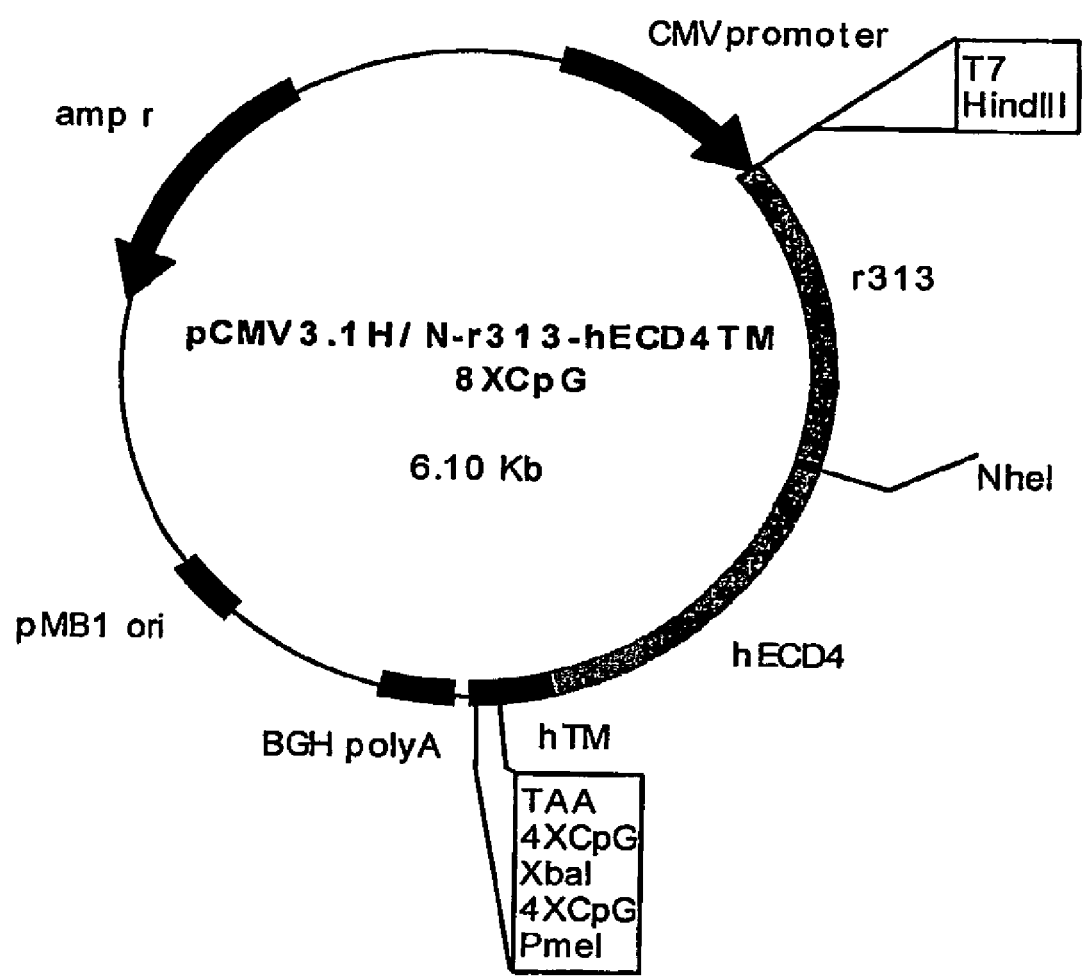
Figure 14:
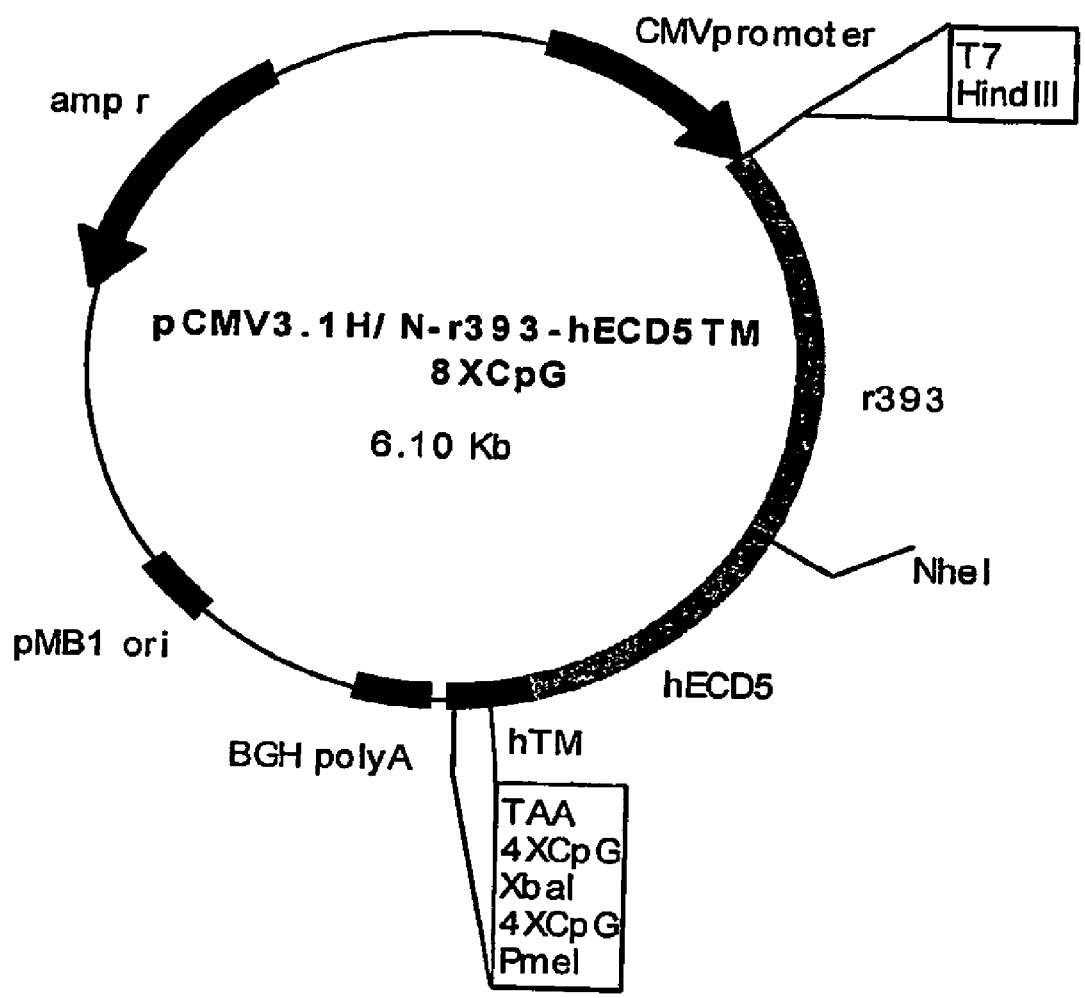

The chimeric proteins differ for human p185$^{neu}$ decreasing portions and rat p185$^{neu}$ increasing portions. Plasmid pCMV3.1H/Nr73-hECD1-TM-8 CpG (FIG. 10) encodes 73 aa of the rat p185$^{neu}$ extracellular domain and 614 aa of human p185$^{neu}$. Plasmid pCMV3.1H/Nr153-hECD2-TM-8CpG (FIG. 11) encodes 153 aa of the rat p185$^{neu}$ extracellular domain and 534 aa of human p185$^{neu}$. Plasmid pCMV3.1H/Nr233-hECD3-TM-8 CpG (FIG. 12) encodes 233 aa of the rat p185$^{neu}$ extracellular domain and 454 aa of human p185$^{neu}$. Plasmid pCMV3.1H/Nr313-hECD4-TM-8 CpG (FIG. 13) encodes 313 aa of the rat p185$^{neu}$ extracellular domain and 374 aa of human p185$^{neu}$. Plasmid pCMV3.1H/Nr393-hECD5-TM-8 CpG (FIG. 14) encodes 393 aa of the rat p185$^{neu}$ extracellular domain and 294 aa of human p185$^{neu}$. Indirect evidence of the membrane expression of human/rat chimeric p185$^{neu}$ encoded by these plasmids has been obtained immunizing mice with the five new plasmids and with pCMV3.1H/N-r1°cys-h2°cysTM-8 CpG as positive control. The sera of all vaccinated mice contain specific antibodies against human p185$^{neu}$. Moreover, the animals vaccinated with plasmids encoding the five different chimeric proteins are also protected with a lethal inoculum of tumour cells expressing human p185$^{neu}$.

EXAMPLES

Example 1

Construction of Plasmid pCMV3.1H/N-r1°cys-h2°cysTM-8 CpG

To construct chimeric plasmid pCMV3.1H/N-r1°cys-h2°cysTM-8 CpG we started from plasmid pCMV-ECD-TM, which expresses the extracellular and transmembrane domain of rat p185$^{neu}$ (Amici et al 2000, Gene Ther., 7: 703). pCMV-ECD-TM was digested with restriction enzymes HindIII and XbaI (BioLabs, Beverly, Mass.) to separate the insert from the plasmid backbone.

Restriction Digestion with EnzymeHindIII:

| plasmid DNA (1 μg/μl) | 10 μl |
|---|---|
| restriction buffer 10X (NEB2) | 10 μl |
| HindIII (10 U/μl) | 5 μl |
| H$_2$O | 75 μl |
| | 100 μl final volume |

The mixture was incubated at 37° C. for 4 hours and the digestion product controlled by electrophoresis on 1% agarose gel using a molecular weight marker and undigested plasmid as control.

Once confirmed plasmid linearization, DNA was precipitated by adding $\frac{1}{10}$ volume of 3 M sodium acetate at pH 5.2 and 2 volumes of cold absolute ethanol.

The sample was kept on ice for 20 min., then centrifugated with a minicentrifuge at 14.000 rpm for 12 min. The pellet was washed three times with 1 ml 70% cold ethanol, dried under vacuum for 5 min, then resuspended in 84 μl H$_2$O and enzymatically digested with restriction enzyme XbaI.

Restriction Digestion with Enzyme XbaI:

| DNA resuspended in H$_2$O (10 μg) | 84 μl |
|---|---|
| Restriction buffer 10X (NEB2) | 10 μl |
| BSA 100X (100 mg/ml) | 1 μl |
| XbaI (10 U/ml) | 5 μl |
| | 100 μl |

The mixture was incubated at 37° C. for 4 hours and the digestion product was precipitated and dried as described above. DNA was resuspended in 30 μl H$_2$O.

The two DNA fragments corresponding to the plasmid backbone (pCMV of 4400 bp) and to the insert (ECD-TM of 2100 bp) were separated by electrophoresis on a 1% agarose gel.

The band corresponding to the insert was removed and DNA eluted from the gel using a Qiaquick gel extraction kit (Qiagen Italy).

In parallel, the new plasmid backbone (pCMV3.1H/N-4 CpG) wherein the DNA fragment corresponding to rat p185 ECD-TM, was digested with the same restriction enzymes and eluted on agarose gel.

The DNA fragments corresponding to rat ECD-TM and the linearized plasmid pCMV3.1H/N-4 CpG were used to obtain pCMV3.1H/N-rECD-TM-4 CpG by ligation reaction.

Ligation Reaction

| DNA insert (rECD-TM) (50 ng/μl) | 2 μl |
|---|---|
| Linearized plasmid DNA (pCMV3.1H/N4CpG) (50 ng/μl) | 1 μl |
| Reaction buffer 10X for T4 DNA ligase | 1 μl |
| T4 DNA ligase (2 U/μl) | 1 μl |
| H$_2$O | 5 μl |
| | 10 μl |

The ligation reaction was incubated at 16° C. for 4 hours.

The ligation product was then used to transform the *E. coli* bacterial strain DH5 α. The bacterial cells have been made competent with the CaCl$_2$ technique.

Transformation of the Bacterial Strain DH5 α:

| Competent bacterial cells | 100 μl |
|---|---|
| Ligation product | 5 μl |

To make the plasmid DNA penetrate the competent cells, these were kept on ice for 40 min. and submitted to thermal shock (1.5 min. at 42° C. and then 2 min. on ice).

After adding 1 ml LB growth medium, the transformed bacterial cells were incubated at 37° C. for 1 hour to restore their physiological conditions.

The cell suspension was then centrifuged at 6000 rpm for 1 min. and the pellet was resuspended in 100 μl LB.

The cells were seeded in Petri dishes containing selective solid medium (LB with agar+ampicillin 100 μg/ml) and grown at 37° C. for 1 night. Ampicillin allows the growth of cells containing plasmid pCMV3.1H/N-rECD-TM-4 CpG which confers ampicillin-resistance.

The resulting clones were analysed by alkaline lysis to select those containing the recombinant plasmid pCMV3.1H/N-rECD-TM-4 CpG.

To obtain chimeric plasmid pCMV3.1H/N-r1°cys-h2°cysTM-8 CpG, plasmid pCMV3.1H/N-rECD-TM-4 CpG was digested with restriction enzymes BstEII and XbaI to remove the second cystein domain together with the transmembrane domain of rat p185$^{neu}$. At the same time, plamid pCMV3.1hECD-TM-4 CpG was digested with the same enzymes to isolate the DNA fragment corresponding to the second cystein subdomain and transmembrane domain of the human gene.

Digestion with BstEII:

| plasmid DNA (1 μg/μl) | 10 μl |
|---|---|
| Restriction buffer 10X (NEB3) | 10 μl |
| BstEII (10 U/μl) | 5 μl |
| H$_2$O | 75 μl |
| | 100 μl final volume |

The mixture was incubated at 60° C. for 4 hours.

Restriction digestion with XbaI, recovery of the fragments to be used for cloning, ligation reaction and transformation of competent cells have been described previously.

The resulting chimeric plasmid pCMV3.1H/N-r1°cys-h2°cysTM-8 CpG has been sequenced using the automatic ABI PRISM 310 Genetic Analyzer (Applied Biosystem), to verify the correct insertion of the fragment corresponding to the 2$^{nd}$ cystein subdomain and the transmembrane domain of the human gene.

Example 2

In Vivo Test

Animals

Balb/cAnCr (H-2$^d$) female mice aged about seven weeks have been used for all experiments.

The animals, supplied by Charles River Laboratories (Calco, MI, Italy), are grown in aseptic conditions and in accordance with the European Community guidelines.

Intramuscular Administration Followed by In Vivo Electroporation

To avoid unwanted contractions of the tibial muscle each mouse was anaesthetized by i.p. inoculum of 300 µl avertine, made of 0.58 g tribromoethanol (Sigma-Aldrich) and 310 µl Tert-Amyl alcohol (Aldrich) dissolved in 39.5 ml deionized H$_2$O. All mice have been then shaved in correspondence of the tibial muscle for the inoculum.

The animals have been vaccinated in correspondence of both antero-tibial muscles, with 40 µl of solution containing 50 µg DNA.

The DNA-containing mixture was prepared shortly before use, in conformity with the indications of Dr. F. Pericle (Valentis, Inc., The Woodlands, Tex., USA). This solution contains 1.25 mg/ml plasmid DNA, 6 mg/ml poly-L-glutamate sodium salt (Sigma-Aldrich, S.r.l., Milano, Italia), 150 mM sodium chloride (Fluka, BioChemika, Buchs, Switzerland) and distilled water free from endotoxins (Nucleare Free Water, Promega Corporation) to a final volume of 1 ml.

After about 5 min from the inoculum, the treated area was submitted to electroporation, by application of two electric impulses having an intensity of 375 V/cm$^2$, each lasting 25 ms, using the electroporator Electro Square Porator (T820, BTX, San Diego, Calif., USA). The transcutaneous electric impulses have been applied by use of two square steel electrodes placed at mm from each other, beside each paw. Gene immunization by electroporation was carried out twice for each animal 21 and 7 days before inoculum of tumour cells.

Inoculum of Tumour Cells

The mice have been inoculated with a suspension containing 2×10$^5$ D2F2/E2 cells. These cells derive from a mammary tumour spontaneously generated in a hyperplastic alveolar node of a BALB/c mouse and express high levels of human p185.

In Vivo Evaluation of Tumour Growth

Tumour growth was evaluated weekly by palpation and the dimensions of the tumours were measured along two perpendicular diameters with a calibre. Neoplastic masses measuring more than 3 mm are considered as tumours.

Tumour growth was followed for 100 days from tumour inoculum or until the tumour had grown to a diameter higher than 10 mm, then animals were sacrificed.

TABLE

Mice: female BALB/c
Tumour: D2F2-E2 espressing human p185$^{neu}$

| plasmids | Number of mice | protection | antibodies |
|---|---|---|---|
| pCMV3.1H/N-8CpG | 5 | 0% | − |
| pCMV3.1H/N-hECD-TM-8CpG | 5 | 100% | +++ |
| pCMV3.1H/N-hECD1-TM-8CpG | 5 | 100% | − |
| pCMV3.1H/N-hECD2-TM-8CpG | 5 | 100% | − |
| pCMV3.1H/N-hECD3-TM-8CpG | 5 | 100% | + |
| pCMV3.1H/N-hECD4-TM-8CpG | 5 | 100% | ++ |
| pCMV3.1H/N-hECD5-TM-8CpG | 5 | 60% | − |
| pCMV3.1H/N-hECD6-TM-8CpG | 5 | 0% | − |
| pCMV3.1H/N-hECD7-TM-8CpG | 5 | 0% | − |
| pCMV3.1H/N-r1°cys-h2°cys.-TM-8CpG | 5 | 100% | +++ |

List of Oligonucleotides Synthesized and Used for Plasmid Construction

```
#1. AccIII-TAA-4CpG-erbB2 sense 71 nt
                                              (SEQ ID NO: 15)
5'CCGGAAGTAAATAATCGACGTTCAAATAATCGACGTTCAAATAATCG

ACGTTCAAATAATCGACGTTCAAT 3'

#2. XbaI-TAA-4CpG-erbB2 antisense 71 nt
                                              (SEQ ID NO: 16)
5'CTAGATTGAACGTCGATTATTTGAACGTCGATTATTTGAACGTCGAT

TATTTGAACGTCGATTATTTACTT 3'

#3. AccIII-TAA-4noCpG-erbB2 sense 71 nt
                                              (SEQ ID NO: 17)
5'CCGGAAGTAAATAATAGAGCTTCAAATAATAGAGCTTCAAATAATAG

AGCTTCAAATAATAGAGCTTCAAT 3'

#4. XbaI-TAA-4noCpG-erbB2 antisense 71 nt
                                              (SEQ ID NO: 18)
5'CTAGATTGAAGCTCTATTATTTGAAGCTCTATTATTTGAAGCTCTAT

TATTTGAAGCTCTATTATTTACTT 3'

#5. HindIII-NheI sense 27 nt
                                              (SEQ ID NO: 19)
5' CTAGGAAGCTTGTTTAACTTGCTAGCT 3'

#6. HindIII-NheI antisense 27 nt
                                              (SEQ ID NO: 20)
5'AGCTAGCTAGCAAGTTAAACAAGCTTC 3'

#7. XbaI-4CpG-neu sense 68 nt
                                              (SEQ ID NO: 21)
5'CTAGATAATCGACGTTCAAATAATCGACGTTCAAATAATCGACGTTC

AAATAATCGACGTTCAAGTTT 3'

#8. PmeI-CpG-neu antisense 64 nt
                                              (SEQ ID NO: 22)
5'AAACTTGAACGTCGATTATTTGAACGTCGATTATTTGAACGTCGATT

ATTTGAACGTCGATTAT 3'

#9. XbaI-4noCpG-neu sense 68 nt
                                              (SEQ ID NO: 23)
5'CTAGATAATAGAGCTTCAAATAATAGAGCTTCAAATAATAGAGCTTC

AAATAATAGAGCTTCAAGTTT 3'

#10. PmeI-4noCpG-neu antisense 64 nt
                                              (SEQ ID NO: 24)
5'AAACTTGAAGCTCTATTATTTGAAGCTCTATTATTTGAAGCTCTATT

ATTTGAAGCTCTATTAT 3'

#11. T7 primer
                                              (SEQ ID NO: 25)
5'TAATACGACTCACTATAGGG 3'

#12. BstEII-neuleader antisense 32 nt
                                              (SEQ ID NO: 26)
5'GGCCGGTTACCCGCGATTCCGGGGGGCAGGAG 3'

#13. hECD1-TM-sense-NheI 35 nt
                                              (SEQ ID NO: 27)
5'CCGGCTAGCTAGCCTGTCCTTCCTGCAGGATATCC 3'

#14. hECD2-TM-sense-NheI 35 nt
                                              (SEQ ID NO: 28)
5'CCGGCTAGCTAGCGGAGGGGTCTTGATCCAGCGGA 3'

#15. hECD3-TM-sense-NheI 35 nt
                                              (SEQ ID NO: 29)
5'CCGGCTAGCTAGCCTGCCCACTGACTGCTGCCATG 3'

#16. hECD4-TM-sense-NheI 35 nt
```

-continued

17. hECD5-TM-sense NheI 35 nt
(SEQ ID NO: 31)
5'CCGGCTAGCTAGCCCGCTCCAGCCAGAGCAGCTCC 3'

18. hECD6-TM-sense-NheI 35 nt
(SEQ ID NO: 32)
5'CCGGCTAGCTAGCAACACCCACCTCTGCTTCGTGC 3'

19. hECD7-TM-sense-NheI 35 nt
(SEQ ID NO: 33)
CCGGCTAGCTAGCCCCAGGGAGTATGTGAATGCCA 3'

20. pcDNA3.1/BGH Reverse primer 20 nt
(SEQ ID NO: 34)
5'TAGAAGGCACAGTCGAGGCT 3'

21. NheI-neuleader-antisense 43 nt
(SEQ ID NO: 35)
5'CCGGCTAGCTAGCCGCGATTCCGGGGGGCAGGAGGGCGAGGAG 3'

22. His-myc-sense-noNheI 69 nt
(SEQ ID NO: 36)
5'CTAGGCATCATCATCATCATCATAATGGTCATACCGGTGAAC

AAAAACTCATCTCAGAAGAGGATCTGG 3'

23. His-myc-antisense-NheI 69 nt
(SEQ ID NO: 37)
5'CTAGCCAGATCCTCTTCTGAGATGAGTTTTTGTTCACCGGTAT

GACCATTATGATGATGATGATGATGC 3'

24. NheI-73neu antisense 35 nt
(SEQ ID NO: 38)
5'CCGGCTAGCTAGCGCTGGCATTGGCAGGCACGTAG 3'

25. NheI-153neu antisense 35 nt
(SEQ ID NO: 39)
5'CCGGCTAGCTAGCCAGGATCTCTGTGAGACTTCGA 3'

26. NheI-233neu antisense 35 nt
(SEQ ID NO: 40)
5'CCGGCTAGCTAGCGCCCTTGCACCGGGCACAACCA 3'

27. NheI-313neu antisense 35 nt
(SEQ ID NO: 41)
5'CCGGCTAGCTAGCTCCCACTTCCGTAGACAGGTAG 3'

28. NheI-393neu antisense 35 nt
(SEQ ID NO: 42)
5'CCGGCTAGCTAGCAATGCCGGAGGAGGGGTCCCCA 3'

The invention claimed is:

1. A method for inhibiting the formation of a p185$^{neu}$ positive tumor in a subject, comprising administering to the subject an effective amount of a DNA transfer vector, the vector comprising at least one of the nucleotide sequences selected from the group consisting of SEQ ID NO: 2, 12, 13 and 14, the nucleotide sequence being under control of a transcription promoter.

2. The method of claim 1, wherein the DNA transfer vector further comprises 4 CpG motifs.

3. The method of claim 1, wherein the DNA transfer vector further comprises 8 CpG motifs.

4. The method of claim 1, comprising administering the DNA transfer vector in a mixture comprising a pharmaceutically acceptable vehicle.

5. The method of claim 1, wherein the DNA transfer vector is administered parenterally.

6. The method of claim 1, wherein the vector comprises the nucleotide sequence SEQ ID NO: 2.

7. The method of claim 1, wherein the vector comprises the nucleotide sequence SEQ ID NO: 12.

8. The method of claim 1, wherein the vector comprises the nucleotide sequence SEQ ID NO: 13.

9. The method of claim 1, wherein the vector comprises the nucleotide sequence SEQ ID NO: 14.

10. The method of claim 1, wherein the p185$^{neu}$ positive tumor is a mammary tumor.

11. The method of claim 1, wherein administering the effective amount of the DNA transfer vector induces a production of antibodies against human p185$^{neu}$ in the subject.

* * * * *